US00RE39760E

(19) United States
(12) Reissued Patent
Tsang et al.

(10) Patent Number: US RE39,760 E
(45) Date of Reissued Patent: Aug. 7, 2007

(54) MONOCLONAL ANTIBODIES AGAINST HUMAN COLON CARCINOMA-ASSOCIATED ANTIGENS AND USES THEREFOR

(75) Inventors: Kwong Y. Tsang, Bethesda, MD (US); Myron Arlen, Great Neck, NY (US)

(73) Assignee: International Bio-Immune Systems Inc., Great Neck, NY (US)

(21) Appl. No.: 09/633,034

(22) Filed: Aug. 4, 2000

Related U.S. Patent Documents

Reissue of:
(64) Patent No.: 5,688,657
Issued: Nov. 18, 1997
Appl. No.: 08/304,524
Filed: Sep. 12, 1994

U.S. Applications:
(63) Continuation-in-part of application No. 08/159,836, filed on Nov. 30, 1993, now abandoned, which is a continuation-in-part of application No. 08/117,430, filed on Sep. 7, 1993, now abandoned, which is a continuation-in-part of application No. 07/670,816, filed on Mar. 18, 1991, now abandoned, which is a continuation-in-part of application No. 07/176,337, filed on Mar. 31, 1988, now abandoned.

(51) Int. Cl.
*G01N 33/574* (2006.01)
*G01N 33/53* (2006.01)
*C07K 16/30* (2006.01)
*C07K 16/18* (2006.01)

(52) U.S. Cl. ..... 435/7.23; 435/7.1; 435/7.2; 435/40.51; 435/40.52; 435/325; 435/328; 435/329; 435/330; 435/332; 435/344; 530/388.8; 530/387.1; 530/387.3; 530/387.5; 530/387.7; 530/388.1; 530/391.1; 530/391.3; 530/391.7

(58) Field of Classification Search ..... 530/388.8, 530/387.1, 387.3, 387.5, 387.7, 388.1, 391.1, 530/391.3, 391.7; 435/7.1, 7.2, 40.51, 40.52, 435/325, 328, 329, 330, 332, 347, 7.91, 7.92, 435/188
See application file for complete search history.

(56) References Cited

U.S. PATENT DOCUMENTS

| | | | | |
|---|---|---|---|---|
| 4,579,827 | A | 4/1986 | Sakamoto et al. | 436/536 |
| 4,699,880 | A | 10/1987 | Goldstein | 435/172.2 |
| 4,703,004 | A * | 10/1987 | Hopp et al. | |
| 4,810,781 | A | 3/1989 | Hollinshead | 530/413 |
| 5,160,723 | A | 11/1992 | Welt et al. | |
| 5,270,202 | A * | 12/1993 | Raychaudhuri | |
| 5,643,550 | A | 7/1997 | Welt et al. | |
| 5,712,369 | A | 1/1998 | Old et al. | |
| 5,958,412 | A | 9/1999 | Welt et al. | |
| 6,235,280 | B1 * | 5/2001 | Chatterjee | |
| 6,342,587 | B1 | 1/2002 | Barbas, III et al. | |
| 6,346,249 | B1 | 2/2002 | Barbas, III et al. | |

FOREIGN PATENT DOCUMENTS

WO WO 86/01533 * 3/1986

OTHER PUBLICATIONS

Koprowski et al PNAS 74:2985–2988, 1977.*
Paul Fundamental Immunology Raven Press, NY, Chapter 8 p. 242, 1993.*
Harlow et al., Antibodies, A Laboratory Manual, Cold Spring Harbor Laboratory, pp. 61, 67, 71, 92–93, 1988.*
Hollinshead et al ., Cancer 56:480–89, 1985.*
Herlyn et al., PNAs 76:1138, 1979.*
Price etal., IRCS Journal of Medical Science 13:366, 1985.*
Nakao et al., 1997 Am J Gastroenterol. Clinical application of a new monoclonal antibody (19B7) against PIVKA–II in the diagnosis of hepatocellular carcinoma and pancreatobiliary malignancies. 92(6):1031–4.
Wolf et al., 1993, J. Immunol. 150(8):p142A; Abstract No. 806 Immunohistological and Flowcytometry studies using monoclonal antibody.
Wolf et al., 1993, Immunoreactivity of cell lines and colon carcinomas with monoclonal antibodies PCA 31.1 and PCA 33.28. Mol. Biol. Cell 4 (supp): p334A; Abstract 1940.
Wolf et al., 1993, Monoclonal antibody 31.1 may differentiate indolent from aggressive colon cancer. Proc. Am. Assoc. Cancer Res. 34: p452 ; Abstract 2695.
Hurwitz et al., 1992, Immunotargeting of a Daunomycin to localized and metastatic human colon adenocarcinoma in athymic mice. Cancer Immunol. Immunother. 35:186–192.
Kuroki et al., 1992, Reaction profiles of seven enzyme immunoassay kits for carcinoembryonic antigen (CEA) analysed with purified preparations of CEA and related normal antigens. Clin. Biochem. 25:29–35.
Bartal et al., 1990, Monoclonal antibody defining an antigen present within a purified tumor membrane vaccine proc. American Assoc. Cancer Res. 31: p260, Abstract No. 1537.
Tsang, 1987, Monoclonal antibodies to human colon carcinoma–associated antigens FASEB 46(3):1058, Abstract No. 4322.
Hughes et al., (1986) Antigen expression in normal and neoplastic colonic mucosa: three tissue–specific antigens using monoclonal antibodies to isolated colonic glands. Cancer Res. 46:2164–2171 (§).

(Continued)

*Primary Examiner*—Sheela J. Huff
(74) *Attorney, Agent, or Firm*—Baker Botts LLP

(57) ABSTRACT

Monoclonal antibodies, in particular 33.28 and 31.1, and chimeric antibodies, in particular mouse/humans chimeric Chi #1 specific for glycoprotein antigens of colon carcinoma-associated antigens which are immunogenic in humans, are disclosed. Such antibodies, and fragments and derivatives thereof, are useful in immunodiagnosis and immunotherapy of human colon, breast, and ovarian cancer, and for purification of antigens which can serve as immunotherapeutic agents. Methods of detecting the colon carcinoma-associated antigen in a sample, and methods for treating subjects having colon, breast, and ovarian carcinomas are disclosed.

28 Claims, 4 Drawing Sheets

OTHER PUBLICATIONS

Proc. Am. Assoc. Cancer Res. 1994, Mar. vol. 35, Abstract 103, "Comparison of immunostaining of colonic neoplasms with PCA 31.1, PCA 33.28, B72–3 and anti–CEA monoclonal antibodies". A.H. Bartal, J. Wolf, H. Lichtig, E. Agranovsky, R. Levy, H. Kerner, V. Bychkov, O. Saric, M. Wolff, Y. Hirshaut, M. Monizur, M. Arlen and L. Pertschuk.
J. Surg. Oncol. 1993, vol. 54, pp. 103–108, "Monoclonal Antibodies and Their Role in Modulation of the Immune Response", Myron Arlen, J.D. and Kwong Y. Tsang, Ph.D.
Ann. New York Acad Sci 1993, vol. 690, pp. 374–375; "Identification and Characterization of a Colon Tumor–Associated Antigen". M. Arlen, A. C. Hollinshead and K. Y Tsang.
Antib. Immunoconjug. Radiopharm 1991, vol. 4, pp. 895–905; "Monoclonal Antibodies to Immunoreactive Tumor Associated Antigen (TAA) from Human Colon Carcinoma". M. Arlen, K.Y. Tsang, A. Bartal, J. Wolf and O. Saric.
FASEB J, 1991, vol. J5, No. 4, Abstract 2109; "Construction of a Mouse/Human Chimeric Light Chain From Murine Monoclonal Antibody 33.28 Against Colorectal Carcinoma–Associated Antigens". D.L. Xu, S. Wei, K.Y. Tsang.
) J. Tumor Marker Oncol. 1990, Vol. 5, No. 4, pp. 313–319; "The Nature of the Monoclonal Antibodies Derived from Immunogenic Membrane Antigen of Human Colon Carcinoma Origin". Myron Arlen and Alfred K. Tsang.
FASEB J., 1988, vol. J2, No. 5, Abstract 6815; "Colon Carcinoma Associated Antigens Characterized by Monoclonal Antibodies". Kwong Y. Tsang, M.F. LaVia, L. Bishop, D.L. Xu, E. Johnson and M. Arlen.
Bartal, A. H et al, Proc. Am Assoc. Can Res, 31:260 (Ast#1537), Mar. 1990.
Price, M.R et al, IRCS J Med Sci, 13(4):366–367, Apr. 1985.
Herlyn, M et al, PNAS, 76(3):1438–1442, Mar. 1979.
Tsang, K.Y. et al, Fed Proc, 46(3):1058 (Abs#4322), Mar. 1987.
Xu, Danlin, Dissertation (Degree 1990) order #9109383, pp. 1–86, 1990.
Kanellos, J et al, JNCI, 75(2):319–332, Aug. 1985.
Shaw, D.R et al, J Immunol, 138:4534–4538, Jun. 15, 1987.
Tsang, K.Y et al, FASEB, J2(5):A6815, 1988.
Hollinshead, A., et al., Science. 177: 887–889 (1972).
Von Kleist, S., et al., Proc. Natl. Acad. Sci. USA 69: 2492–2494 (1972).
Hollinshead, A.C., J. Nat. Cancer Instit. 52: 327–338 (1974).
Hollinshead, A.C., Cancer, 34: 1235–1243 (1974).
Hollinshead, A.C., Lung Cancer Progress in Therapeutic Research, pp. 501–520, Muggia, F., Rosencweig, M. (ed.), Raven Press, 1979, no date.
Herlyn, M., et al. Proc. Natl. Acad. Sci. USA 79: 1438–1442 (1979).
Hollinshead, A. et al., Tumor Progression, pp. 289–300, Crispen (ed) (1980).
Herlyn, M., et al. J. Clinical Immunol. 2: 135–140 (1982).
Hollinshead, A.C., et al., Cancer 49: 1387–1404 (1982).
Moldofsky, P.J., et al., Radiology 149: 549–555 (1983).
Buchegger, F., et al., J. Experimental Medicine 158: 413–427 (1983).
Takita, J., et al., Cancer Immunol. Immunother. 20:231–235 (1985).
Price, M.R., et al., IRCS Med. Sci. 13: 366–367 (1985).
Kanellos, J., et al., JNCI 75: 319–332 (1985).
Hollinshead, A., et al., Cancer 56: 480–489 (1985).
Stewart, T.H.M., et al., Lung Cancer: Current Status and Prospects for the Future—Ann. Clin. Conf. on Cancer 28:351–374, 1986, no date.
Tsang, K., et al., JNIC 77: 1175–1180 (1986).
Douillard, J.Y., et al., Hybridoma 5: 5139–5149 (1986).
Hollinshead, A., Biologic Drugs, Vaccines, Current Status and Future Directions, pp. 86–103, Springer Verlag (1986).
Tsang, K., et al., Fed Proc. 46:4322 (1987).
Shaw, D.R., et al., J. Immunology 138: 4532–4538 (1987).
Tsang, K., et al., Cancer Detection and Prevention 11: 094 (1987).
Greiner, J.W., et al., Science 235: 895–898 (1987).
Tsang, K., et al., Fed. Proc. 6815 (1988).
Tsang, K., et al., 7th International Congress of Immunology, Abstract 125–46 (1989).
Bartel, A., et al., Proceedings 31: Abstract 1537 (1990).
Arlen, M. and Tsang, K., J. Tumor Marker Oncology 5: 313–319 (1990).
Hirschfield, L.S., et al., Federation of American Societies for Experimental Biology, Abstract 5708 (1991).
Xu, D.L., et al., Fed. Amer. Soc. Exper. Biol., Abstract 2109 (1991).
Hollinshead, A.C. and Stewart, T.H.M., Yale Journal of Biology and Medicine 54: 367–379 (1981).
Sears, H.F., et al., J. Clinical Immunol. 2: 141–149 (1982).
Arlen, M., et al., Antibody, Immunoconjugates, and Radiopharmaceuticals, 4: 895–905 (1991).
Arlen, M., et al., Journal of Surgical Oncology 54: 103–108 (1991).
Arlen, M., et al., NY Academy (cancer vaccines) 603–605 (1993).
Fernado, A.D. et al., Miami Symp. Short Reports 3: 88 (1993).
Girardet, C., et al., J. Immunology 136: 1497–1503 (1986).
Chong, G., F. T. Lee, et al. (2005). "Phase I Trial of 131I–huA33 in Patients with Advanced Colorectal Carcinoma." Clin Cancer Res 11(13): 4818–26.
Koppe, M. J., R. P. Bleichrodt, et al. (2005). "Radioimmunotherapy and colorectal cancer." Br J Surg 92(3): 264–276.
Mallegol, J., G. van Niel, et al. (2005). "Phenotypic and functional characterization of intestinal epithelial exosomes." Blood Cells Mol Dis 35(1): 11–16.
Scott, A. M., F. T. Lee, et al. (2005). "A Phase I Trial of Humanized Monoclonal Antibody A33 in Patients with Colorectal Carcinoma: Biodistribution, Pharmacokinetics, and Quantitative Tumor Uptake." Clin Cancer Res 11(13): 4810–4817.
Deckert, P. M., W. G. Bornmann, et al. (2004). "Specific tumour localisation of a huA33 antibody—carboxypeptidase A conjugate and activation of methotrexate–phenylalanine." Int J Oncol 24(5): 1289–95.
Joosten, C. E., L. S. Cohen, et al. (2004). "Glycosylation profiles of the human colorectal cancer A33 antigen naturally expressed in the human colorectal cancer cell line SW1222 and expressed as recombinant protein in different insect cell lines." Biotechnol Prog 20(4): 1273–9.
Deckert, P. M., C. Renner, et al. (2003). "A33scFv–cytosine deaminase: a recombinant protein construct for antibody–directed enzyme–prodrug therapy." Br J Cancer 88(6): 937–9.
Mao, Z., S. Song, et al. (2003). "Transcriptional regulation of A33 antigen expression by gut–enriched Kruppel like factor." Oncogene 22(28):4434–43.
Welt et al., 2003, Phase I Study of Anticolon Cancer Humanized Antibody A331. Clinical Cancer Res. 9(4):1338:1346.
Welt, S., G. Ritter, et al. (2003). "Preliminary report of a phase I study of combination chemotherapy and humanized A33 antibody immunotherapy in patients with advanced colorectal cancer." Clin Cancer Res 9(4): 1347–53.

Johnstone, C. N., S. J. White, et al. (2002). "Analysis of the regulation of the A33 antigen gene reveals intestine–specific mechanisms of gene expression." J Biol Chem 277(37): 34531–9.
Orlova, A., J. Hoglund, et al. (2002). "Comparative biodistribution of the radiohalogenated (Br, I and At) antibody A33. Implications for in vivo dosimetry." Cancer Biother Radiopharm 17(4): 385–96.
van Niel, G. and M. Heyman (2002). "The epithelial cell cytoskeleton and intracellular trafficking. II. Intestinal epithelial cell exosomes: perspectives on their structure and function." Am J Physiol Gastrointest Liver Physiol 283(2): G251–5.
Barendswaard, E. C., J. L. Humm, et al. (2001). "Relative therapeutic efficacy of (125)I– and (131)I–labeled monoclonal antibody A33 in a human colon cancer xenograft." J Nucl Med 42(8): 1251–6.
Lee, F. T., A. Rigopoulos, et al. (2001). "Specific localization, gamma camera imaging, and intracellular trafficking of radiolabelled chimeric anti–G(D3) and ganglioside monoclonal antibody KM871 in SK–MEL–28 melanoma xenografts." Cancer Res 61(11): 4474–82.
Ritter, G., L. S. Cohen, et al. (2001). "Serological analysis of human anti–human antibody responses in colon cancer patients treated with repeated doses of humanized monoclonal antibody A33." Cancer Res 61(18):6851–9.
van Niel, G., G. Raposo, et al. (2001). "Intestinal epithelial cells secrete exosome–like vesicles." Gastroenterology 121(2): 337–49.
Abud, H. E., C. N. Johnstone, et al. (2000). "The murine A33 antigen is expressed at two distinct sites during development, the ICM of the blastocyst and the intestinal epithelium." Mech Dev 98(1–2): 111–4.
Deckert, P. M., A. Jungbluth, et al. (2000). "Pharmacokinetics and microdistribution of polyethylene glycol–modified humanized A33 antibody targeting colon cancer xenografts." Int J Cancer 87(3): 382–90.
Johnstone, C. N., N. C. Tebbutt, et al. (2000). "Characterization of mouse A33 antigen, a definitive marker for basolateral surfaces of intestinal epithelial cells." Am J Physiol Gastrointest Liver Physiol 279(3): G500–10.
Rader, C., G. Ritter, et al. (2000). "The rabbit antibody repertoire as a novel source for the generation of therapeutic human antibodies." J Biol Chem 275(18): 13668–76.
Ruan, S., J. A. O'Donoghue, et al. (2000). "Optimizing the sequence of combination therapy with radiolabeled antibodies and fractionated external beam." J Nucl Med 41(11): 1905–12.
Sakamoto, J., H. Kojima, et al. (2000). "Organ–specific expression of the intestinal epithelium–related antigen A33, a cell surface target for antibody–based imaging and treatment in gastrointestinal cancer." Cancer Chemother Pharmacol 46 Suppl: S27–32.
Barendswaard, E. C., J. A. O'Donoghue, et al. (1999). "131I radioimmunotherapy and fractionated external beam radiotherapy: comparative effectiveness in a human tumor xenograft." J Nucl Med 40(10): 1764–8.
Miyazono, Y., Y. Kamogawa, et al. (1999). "Effect of B7.1–transfected human colon cancer cells on the induction of the autologous tumour–specific cytotoxic T cells." J Gastroenterol Hepatol 14(10): 997–1003.
Barendswaard, E. C., A. M. Scott, et al. (1998). "Rapid and specific targeting of monoclonal antibody A33 to a colon cancer xenograft in nude mice." Int J Oncol 12(1): 45–53.
Burgess, A. W. (1998). "Growth control mechanisms in normal and transformed intestinal cells." Philos Trans R Soc Lond B Biol Sci 353(1370): 903–9.
Moritz, R. L., G. Ritter, et al. (1998). "Micro–sequencing strategies for the human A33 antigen, a novel surface glycoprotein of human gastrointestinal epithelium." J Chromatogr A 789(1–2): 91–101.
Tio, T. L. (1998). "Diagnosis and staging of esophageal carcinoma by endoscopic ultrasonography." Endoscopy 30 Suppl I: A33–40.
Catimel, B., M. Nerrie, et al. (1997). "Kinetic analysis of the interaction between the monoclonal antibody A33 and its colonic epithelial antigen by the use of an optical biosensor. A comparison of immobilisation strategies." J Chromatogr A 776(1): 15–30.
Heath, J. K., S. J. White, et al. (1997). "The human A33 antigen is a transmembrane glycoprotein and a novel member of the immunoglobulin superfamily." Proc Natl Acad Sci USA 94(2): 469–74.
Ji, H., R. L. Moritz, et al. (1997). "Electrophoretic analysis of the novel antigen for the gastrointestinal–specific monoclonal antibody, A33." Electrophoresis 18(3–4): 614–21.
Ritter, G., L. S. Cohen, et al. (1997). "Characterization of posttranslational modifications of human A33 antigen, a novel palmitoylated surface glycoprotein of human gastrointestinal epithelium." Biochem Biophys Res Commun 236(3): 682–6.
Tschmelitsch, J., E. Barendswaard, et al. (1997). "Enhanced antitumor activity of combination radioimmunotherapy (131I–labeled monoclonal antibody A33) with chemotherapy (fluorouracil)." Cancer Res 57(11): 2181–6.
No Author listed. (1996). "MoAb A33 shows promise in targeting colon cancer for radioimmunotherapy." Oncology (Huntingt) 10(4): 553.
Antoniw, P., A. P. Farnsworth, et al. (1996). "Radioimmunotherapy of colorectal carcinoma xenografts in nude mice with yttrium–90 A33 IgG and Tri–Fab (TFM)." Br J Cancer 74(4): 513–24.
Daghighian, F., E. Barendswaard, et al. (1996). "Enhancement of radiation dose to the nucleus by vesicular internalization of iodine–125–labeled A33 monoclonal antibody." J Nucl Med 37(6): 1052–7.
Welt, S., A. M. Scott, et al. (1996). "Phase I/II study of iodine 125–labeled monoclonal antibody A33 in patients with advanced colon cancer." J Clin Oncol 14(6): 1787–97.
King, D. J., P. Antoniw, et al. (1995). "Preparation and preclinical evaluation of humanised A33 immunoconjugates for radioimmunotherapy." Br J Cancer 72(6): 1364–72.
Scott, A. M., E. Rosa, et al. (1995). "In vivo imaging and specific targeting of P–glycoprotein expression in multidrug resistant nude mice xenografts with [125I]MRK–16 monoclonal antibody." Nucl Med Biol 22(4): 497–504.
Welt et al., 1994, Phase I/II Study of Iodine 131–Labeled Monoclonal Antibody A33 in Patients With Advanced Colon Cancer. J. Clin. Oncol. 12:1561–71.

* cited by examiner

MONOCLONAL ANTIBODIES AGAINST HUMAN COLON CARCINOMA-ASSOCIATED ANTIGENS AND USES THEREFOR

Matter enclosed in heavy brackets [ ] appears in the original patent but forms no part of this reissue specification; matter printed in italics indicates the additions made by reissue.

This application is a continuation-in-part of U.S. application Ser. No. 08/159,836 filed Nov. 30, 1993, which is a continuation-in-part of U.S. application Ser. No. 08/117,430, filed Sep. 7, 1993, now abandoned, which is a continuation-in-part of U.S. application Ser. No. 07/670,816, filed Mar. 18, 1991, now abandoned, which is a continuation-in-part of U.S. application Ser. No. 07/176,337, filed Mar. 31, 1988, now abandoned.

BACKGROUND OF THE INVENTION

1. Field of the Invention

This invention, in the field of immunology and medicine, relates to new hybridoma lines and the monoclonal antibodies (mAbs) they secrete which are specific for clinically defined colon carcinoma-associated antigens. The mAbs are useful in vivo for immunodetection and immunotherapy of colon carcinoma as well as for the detection and purification of colon carcinoma-associated antigens.

2. Description of the Background Art

During the process of oncogenesis, a number of cell-surface molecules or markers appear on cells. Such tumor-related markers include oncofetoproteins, neoglycoproteins, sphignolipids, and modifications of existing surface proteins. Such new or altered structures are often shed from the tumor cell surface and appear in the serum or in other biological fluids. The detection of any of these substances or "tumor markers" serves as the basis for diagnosing or monitoring the progress of neoplastic disease.

Early animal studies demonstrated that, among these tumor markers, a subset of tumor membrane protein or glycoprotein antigens were immunogenic. Upon appropriate reintroduction into the tumor-bearing host, typically after surgical removal of the primary tumor, such antigens could effectively block the establishment of new tumor growth.

An attempt to use similarly derived tumor-associated antigens in humans was made by Hollinshead and Stewart using a relatively purified membrane preparation in patients with lung cancer (Stewart, T. H. M. et al., Ann. N.Y. Acad. Sci. 277:436 (1976)). These studies were later expanded to include patients with melanoma and colon carcinoma, wherein different pooled allogeneic tumor preparations were administered in combination with complete Freund's adjuvant (Hollinshead, A. C. et al., Cancer 4:9:1387 (1982); Hollinshead, A. C. et al., Cancer 56:480 (1985)).

The use of Freund's adjuvant was based on observations that normal tissue antigens with this adjuvant produced severe autoimmune responses in animal recipients, whereas in the absence of this adjuvant, no adverse reactions were seen. The adjuvant was thought to promote antigen processing by host macrophages as well as prolong the stimulatory action of the antigen at the site of its deposition (see, for example, Roitt, L. Essential Immunology, 6th Ed., Blackwell Scientific Publications, Oxford (1988)).

The above observations served as the basis for early clinical trials using specific human tumor membrane proteins and glycoproteins as tumor "vaccines." Various of the tumor-associated antigens which had been isolated and characterized could prolong survival and, in some cases, produce regression of metastatic disease.

With the advent of monoclonal antibody (mAb) technology, it has become possible to obtain pure antibody populations which permit better purification and characterization of the various tumor markers and tumor-associated antigens that are useful for immunodiagnosis or immunotherapy. Many mAbs have been described that have varying degrees of selectivity for tumor antigens (versus normal cell surface markers); some of these tumor antigens are broadly represented across several or many tumor types, whereas others appear to be truly tumor-specific. A number of these mAb-tumor antigen systems are described below.

Herlyn et al., Proc. Natl. Acad. Sci. USA 76:1438 (1979), discloses two mAbs obtained by immunizing mice with human colorectal carcinoma (CRC) cells. The mAbs have selective reactivity with human CRC cells. One mAb, 1083–17 (the forerunner of 17-1A), is now known to react with a 41 kDa glycoprotein (see below).

Herlyn et al., J. Clin. Immunol. 2:135 (1982), described the detection of a circulating colorectal carcinoma (CRC)-associated antigen by a mAb developed against a membrane antigen of the SW116 cell line. MAbs 19-9 and 52a, which recognize a monosialoganglioside antigen (Magnani, J. L. et al., Science 212:55 (1981)), reacted with cells of 8 of 12 CRC lines as well as with the cells of one gastric carcinoma and one pancreatic carcinoma. MAb $C_4$14 reacted with four of six CRC cultures and with gastric tumor cells. The binding of mAbs 19-9 and 52a to tumor cells were inhibited by a CRC patient's serum. However, CRC sera inhibited binding less frequently than did sera from patients with pancreatic or gastric tumors.

Girardet et al., J. Immunol. 136:1497–1503 (1986), disclosed mAbs against human colon carcinomas. The L-D1 mAb reacted with a 41 kDa glycoprotein, believed to be the same antigen as that defined by mAb 1083-17-1A (Herlyn et al., 1979, supra). The L-C5 mAb precipitated proteins having molecular weights of 43, 45, 47 and 53 kDa from LoVo colon carcinoma cells. L-D1 did react with cervical carcinoma lines, while L-C5 reacted with breast carcinoma lines. Their binding to pancreatic carcinomas was not examined.

Greiner et al., Science 235:895–898 (1987), discloses mAb 06.2 which reacts with a 90 kDa glycoprotein allegedly found in 75–80% of breast carcinomas and more than 90% of colon carcinomas.

Sakamoto et al., U.S. Pat. No. 4,579,827 (Apr. 1, 1986), discloses a number of mAbs said to be useful for diagnosing or treating human colon cancer by a number of different approaches. None of these mAbs is shown to react with a human colon carcinoma-associated antigen that is a protein of [either] 61 [or 72] kDa molecular weight, distinguishing these antibodies from the [antibodies] *33.28 antibody* of the present invention (described below). Furthermore, none of the Sakamoto mAbs have the degree of colon tumor specificity of the mAbs disclosed in the present application.

Delaloye et. al., J. Clin. Invest. 77:301 (1986), discloses the use of a mAb specific for carcinoembryonic antigen (CEA) to detect colorectal carcinoma in vivo using $^{123}$I-labelled fragments and emission computerized tomography. The mAb described bears no relation to the mAbs of the present invention.

Douillard et al., Hybridoma 5, Suppl. 1:S139 (1986), describes mAb 17-1A and its cytotoxic properties to gastrointestinal adenocarcinomas in vitro. 17-1A was used with some degree of success in immunotherapy trials. This mAb is said to recognize a 38–41 kDa protein and has a broad range of reactivity and lack of colon tumor specificity, clearly distinguishing it from the antibodies of the present invention.

Scannon et al., U.S. Pat. No. 4,590,071 (May 20, 1986), discloses mAbs specific for melanoma antigens conjugated to toxic proteins such as ricin A chain and the use of these compositions to treat melanoma. There is no disclosure directed to colon tumor antigens or antibodies and their uses.

The relatively pure antigen preparation containing the immunogenic colon carcinoma membrane antigens to which the mAbs of the present invention are directed was originally described by Hollinshead et al., Science 177:887–889 (1972).

The clinical evaluation of the above antigen preparation, including a description of its immunogenicity and potential for enhancing patient survival through stimulation of specific active immunity, was described by Hollinshead et al., 1985, supra.

The work of the present inventors leading to the present invention is briefly described in an abstract by Tsang et al., "Monoclonal Antibodies to Human Colon Carcinoma Associated Antigens," Intl. Symp. Biotech. in Clin. Med., Rome, Italy, Apr. 13–15, 1987. This reference was made available to the public less than one year before the filing of the ultimate parent application (U.S. Ser. No. 07/176,337) for the present application.

SUMMARY OF THE INVENTION

The present inventors have produced murine mAbs and mouse-human chimeric antibodies specific for colon carcinoma-associated antigens which were known to be immunogenic in humans. These antigens, isolated in the inventors' laboratory, are unique among the previously described colon cancer antigens in that (1) the epitopes recognized by the mAbs are of the protein and not the carbohydrate component of tumor-associated glycoproteins; (2) the antigens are not expressed in normal tissues; (3) the antigens are tumor-specific, being present in malignancies of colon, breast, and ovarian cancer; (4) the antigens are immunogenic in humans, having the capability of enhancing host anti-tumor immunity by both cellular as well as humoral responses, thus improving survival in cancer patients; and (5) the immunogenicity in humans is specific, in that only colon, breast and ovarian cancer patients, but not patients with other forms of cancer, show evidence of specific in vivo or in vitro immunological reactivity to the antigens.

The mAbs and chimeric antibodies of the present invention are useful for diagnosis or therapy of colon, breast, and ovarian carcinoma, for example by imaging metastatic tumors, by delivering cytotoxic agents to the tumors, and by activating host effector mechanisms such as antibody-dependent cellular cytotoxicity (ADCC) or complement dependent cytotoxicity (CDC) to directly kill tumor cells.

The present invention is thus directed to a monoclonal antibody specific for a human colon carcinoma-associated protein antigen wherein the antigen is specifically immunogenic in humans, and the antigen is not detectable on normal human tissues [or on human carcinoma cells other than colon, breast and ovarian carcinoma cells].

The present invention is also directed to a chimeric antibody specific for a human colon carcinoma-associated protein antigen wherein the antigen is not detectable on normal human tissues [or on human carcinoma cells other than colon carcinoma cells]. Mouse hybridoma PCA 31.1 has been deposited at ATCC *on Sep. 22, 2000* and assigned ATCC [HB-12314] *Accession No. PTA-2497*. Mouse hybridoma PCA 33.28 has been deposited at ATCC *on Aug. 26, 2003* and assigned ATCC [HB-12315] *Accession No. PTA-5413*. Cells transfected with chimeric 31.1 have been deposited at ATCC *on Mar. 13, 1997* and assigned ATCC *Accession No.* CRL-12316. The above deposits [were made] *are maintained* at American Type Culture Collection, [12301 Parklawn Drive, Rockville, Md. 20862 USA on Mar. 13, 1997] *10801 University Boulevard, Manassas, Va. 20110-2209*.

In one embodiment, the antibody is specific for a CCAA which is a protein having a molecular weight of about 61 kilodaltons. [In another embodiment, the antibody is specific for a CCAA which is a protein having a molecular weight of about 72 kilodaltons.] In a preferred embodiment, the antibody is the mouse monoclonal antibody 33.28 or 31.1 or an antibody which binds specifically to the same colon carcinoma-associated epitope as that bound by 33.28 or 31.1. In another preferred embodiment, the antibody is a mouse/human chimeric antibody Chi #1 that binds specifically to the same colon carcinoma-associated epitope as that bound by 31.1.

The present invention is also directed to the above antibody immobilized on a solid phase.

The present invention includes the above antibody delectably labelled, for example, with a radiolabel.

In additional embodiments, the above antibody is conjugated to a cytotoxic radionuclide, a cytotoxic drug, or a cytotoxic protein.

In yet another embodiment, the present invention is directed to monoclonal antibodies against the above antibodies, i.e., second generation monoclonal antibodies.

In a further embodiment, the present invention is directed to third generation monoclonal antibodies, i.e., monoclonal antibodies directed against the above second generation monoclonal antibodies.

The present invention is also directed to the above-discussed colon carcinoma-associated antigens which are unique in that (1) the epitopes recognized by the mAbs are of the protein and not the carbohydrate component of tumor-associated glycoproteins; (2) the antigens are not expressed in normal tissues; (3) the antigens are tumor-specific, being present in the malignancies of colon, breast and ovarian cancer; (4) the antigens are immunogenic in humans, having the capability of enhancing host anti-tumor immunity, thus improving survival in cancer patients; and (5) the immunogenicity in humans is specific, in that only colon, breast and ovarian cancer patients, but not patients with other forms of cancer, show evidence of specific in vivo or in vitro immunological reactivity to the antigens.

To date, all other purified antigens that have been used have failed to elicit both a cellular and a humoral response.

The present invention also provides a pharmaceutical composition useful for the immunotherapy of colon, breast and ovarian cancer comprising an antibody, fragment or derivative, as above, conjugated to a cytotoxic radionuclide, a cytotoxic drug, or a cytotoxic protein, in a suitable excipient.

The present invention includes an immunoassay method for detecting in a sample a colon carcinoma-associated antigen capable of binding to the 33.28 or 31.1 murine monoclonal antibody or Chi #1, comprising:

(a) contacting the sample with an antibody described above; and (b) detecting the antigen by detecting the binding of the antibody.

In another embodiment, the invention provides as imaging method for detecting a colon carcinoma-associated antigen in a subject, comprising:

(a) contacting the detectably labelled antibody as described above with the subject; and (b) detecting the antigen.

The present invention also includes a method of killing cells carrying a colon carcinoma-associated antigen, comprising:

(a) delivering to the cells an antibody as above, and a cytotoxic effector agent; and (b) allowing the killing to occur.

The effector agent may be complement, or effector cells active in ADCC. Alternatively, antibodies labelled conjugated with a cytotoxic radionuclide, drug or protein may be used directly.

The present invention is further directed to a method of treating a subject suspected of having a colon, breast and ovarian carcinoma bearing an antigen which is capable of binding to the 33.28 or 31.1 monoclonal antibody, or Chi #1 chimeric antibody comprising administering to the subject an effective dose of a pharmaceutical composition as described above.

Also provided is a method for producing an immunogenic composition useful for clinical immunotherapy of colon, breast, and ovarian carcinoma, comprising:

(a) preparing a membrane extract of a tumor or cell line bearing an antigen which is capable of binding to the 33.28 or 31.1 monoclonal antibody or Chi #1 antibody; and (b) isolating the antigen by affinity purification using an antibody as described above, thereby producing the immunogenic composition.

In another embodiment, the present invention is directed to the use of the above antigen to produce a vaccine.

The present invention also includes a method of detecting and diagnosing colon, breast and ovarian cancer by staining monoclonal antibody or chimeric antibody bound to the above-described human colon carcinoma-associated antigen.

In another embodiment, the present invention includes a kit for selectively characterizing colon, breast, and ovarian carcinomas.

DESCRIPTION OF THE PREFERRED EMBODIMENTS

Figure 1:
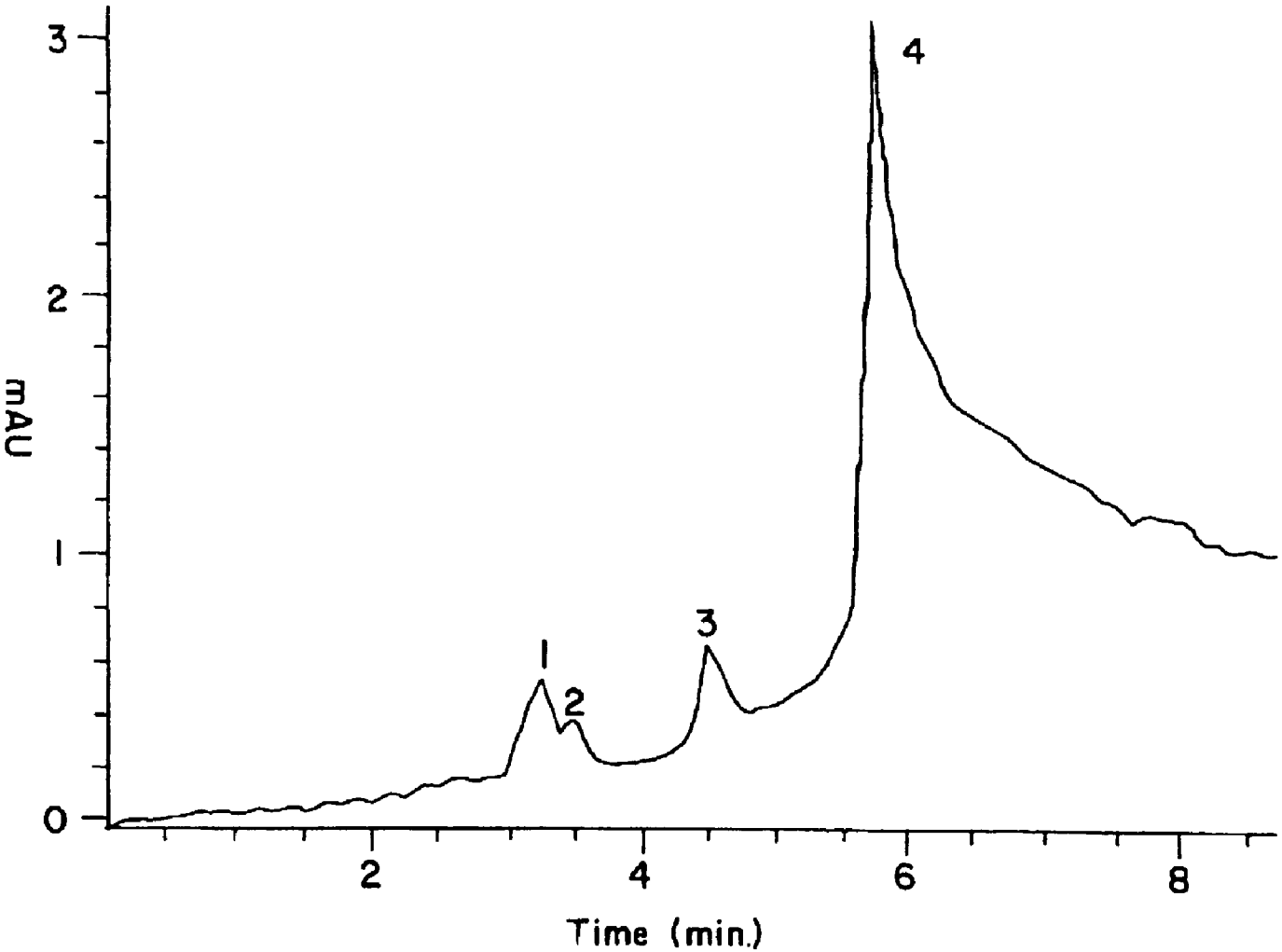
FIG. 1 is a tracing showing an HPLC elution profile of the Hollinshead "vaccine," a partially purified preparation of colon carcinoma cell membranes.

The present invention provides antibodies, including monoclonal and chimeric antibodies, that are specific for, and capable of binding to, immunogenic human colon carcinoma-associated antigens (CCAA) which are protein in nature. These antibodies are useful for diagnostic and therapeutic purposes in subjects having or developing colon, breast or ovarian carcinoma.

The present invention provides not only mouse mAbs, but also chimeric antibodies which are constructed from mouse V regions derived from the mAbs of the present invention. Thus, the chimeric antibodies maintain the ability to recognize the same CCAA epitopes as the mAbs.

The term "epitope" refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The term "antibody" is meant to include both intact immunoglobulin molecules as well as fragments and derivatives thereof, such as, for example, Fab, Fab', $F(ab')_2$ and Fv, which are capable of binding antigen. These fragments lack the Fc fragment of intact antibody, clear more rapidly from the circulation, and may have less non-specific tissue binding than an intact antibody (Wahl et al., J. Nucl. Med. 24:316–325 (1983)). These fragments are produced from intact antibodies using methods well known in the art, for example by proteolytic cleavage with enzymes such as papain (to produce Fab fragments) or pepsin (to produce $F(ab')_2$ fragments).

A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

By "vaccine" is meant an agent used to stimulate the immune system of a living organism so that immunological protection against further harm caused by an infectious agent is provided. Administration of a vaccine contemplated by the present invention to the patient may be by any known or standard techniques. These include oral ingestion, intestinal intubation, or broncho-nasal spraying. Other methods of administration, such as intravenous injection, that allow the carrier microbe to reach the human or animal's bloodstream may be acceptable when the carrier microbe is unable to reproduce.

The antibodies of the present invention are novel in that they are the first known mAbs and chimeric antibody specific for CCAA wherein the tumor antigens are known to be immunogenic in humans. That is, the antigens recognized by the antibodies of the present invention induce an immune response in patients with colon, breast, and ovarian cancer, but not in other individuals, such as patients with other types of cancer. The immunogenicity of these antigens is expressed chiefly as cell-mediated immunity, measurable either by assay of delayed cutaneous hypersensitivity in vivo ("skin tests"), or by various in vitro assays of specific lymphocyte reactivity, such as lymphocyte proliferation or lymphocyte migration inhibition assays. For general principles of immunogenicity and description of various assays of specific immunological reactivity, see: Roitt, I., Essential Immunology, 6th Ed., Blackwell Scientific Publications, Oxford (1988); Roitt, I. et al., Immunology, C. V. Mosby Co., St. Louis, Mo. (1985); Klein, J., Immunology, Blackwell Scientific Publications, Inc., Cambridge, Mass. (1990); Klein, J., Immunology: The Science of Self-Nonself Discrimination, John Wiley & Sons, New York, N.Y. (1982); Paterson, P. Y., Textbook of Immunopathology, Grune and Stratton, New York, (1986), which are hereby incorporated by reference.

In a preferred embodiment, the antibody of the present invention is a murine mAb designated 33.28. In another preferred embodiment, the antibody is a murine mAb designated 31.1. In yet another embodiment the antibody is a chimeric antibody which recognizes an epitope recognized by 33.28. In another embedment, the antibody is a chimeric antibody which recognizes an epitope recognized by 31.1.

The chimeric antibodies of the invention comprise individual chimeric heavy (H) and light (L) immunoglobulin chains. The chimeric H chain comprises an antigen-binding region derived from the H chain of a non-human antibody specific for the epitope recognized by 33.28 or 31.1, which is linked to at least a portion of a human H chain C region ($C_H$).

A preferred chimeric L chain comprises an antigen-binding region derived from the L chain of either the 33.28 or 31.1 mAb, linked to at least a portion of a human L chain C region ($C_L$).

Alternatively, a preferred chimeric H chain comprises an antigen-binding region derived from the L chain of either the 33.28 or 31.1 mAb, linked to at least a portion of a human L chain C region ($C_H$).

As used herein, the term "antigen-binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

The invention also provides for "derivatives" of the monoclonal or chimeric antibodies, which term includes those proteins encoded by truncated or modified genes to yield molecular species functionally resembling the immunoglobulin fragments. The modifications include, but are not limited to, addition of genetic sequences coding of cytotoxic proteins such as plant and bacterial toxins. The fragments and derivatives can be produced from prokaryotic or eukaryotic hosts, as described herein by recombinant means. Alternatively, the fragments and derivatives may be produced by chemical means, such as proteolytic cleavage of intact immunoglobulin molecules, or other chemical modifications or derivatizations known in the art. Such derivatized moieties may improve the solubility, absorption, biological half-life, and the like. The moieties may alternatively eliminate or attenuate any undesirable side effect of the antibody protein. Moieties capable of mediating such effects are disclosed, for example, in Remington's Pharmaceutical Sciences, 16th ed., Hack Publishing Co., Easton, Pa. (1980).

Antibodies, fragments or derivatives having chimeric H chains and L chains of the same or different V region binding specificity can be prepared by appropriate association of the individual polypeptide chains, as taught, for example by Sears et al., Proc. Natl. Acad. Sci. USA 72:353∝357 (1975). With this approach, hosts expressing chimeric H chains (or their derivatives) are separately cultured from hosts expressing chimeric L chains (or their derivatives) and the immunoglobulin chains are separately recovered and then associated. Alternatively, the hosts can be co-cultured and the chains allowed to associate spontaneously in the culture medium, followed by recovery of the assembled immunoglobulin, fragment or derivative.

Murine hybridomas which produce mAb specific for CCAA, such as the 33.28 and 31.1 mAbs of the present invention, are formed by the fusion of a mouse fusion partner cell, such as SP2/0, and spleen cells from mice immunized against the CCAA.

Mice may be immunized with crude or semi-purified preparations containing the antigens of interest, such as, for example, the Hollinshead "vaccine," which is a partially purified membrane preparation of colon-carcinoma cells (Hollinshead et al., supra). To immunize the mice, a variety of different conventional protocols may be followed. For example, mice may receive primary and boosting immunizations of antigenic preparations.

The cell fusions are accomplished by standard procedures well known to those skilled in the field of immunology (Kohler and Milstein, Nature 256:495–497 (1975) and U.S. Pat. No. 4,376,110; Hartlow, E. et al., supra; Campbell, A., "Monoclonal Antibody Technology," In: Laboratory Techniques in Biochemistry and Molecular Biology, Volume 13 (Burdon, R., et al., eds. ), Elsevier, Amsterdam (1984); Kennett et al., Monoclonal Antibodies (Kennett et al., eds. pp. 365–367, Plenum Press, N.Y., 1980); de St. Groth, S. F., et al., J. Immunol. Meth. 35:1–21 (1980); Galfre, G. et al., Methods Enzymol. 73:3–46 (1981); Goding, J. W. 1987, Monoclonal Antibodies: Principles and Practice, 2nd ed. Academic Press, London, 1987).

Fusion partner cell lines and methods for fusing and selecting hybridomas and screening for mAbs are well known in the art (Hartlow, E. et al., supra; Kawamoto, T. et al., Meth. Enzymol. 121:266–277 (1986); Kearney, J. F. et al., J. Immunol. 123:1548–1550 (1979); Kilmartin, J. V. et al., J. Cell Biol. 93:576–582 (1982); Kohler, G. et al., Eur. J. Immunol. 6:292–295 (1976); Lane, D. P. et al., J. Immunol. Meth. 47:303–307 (1981); Mueller, U. W. et al., J. Immunol. Meth. 87:193–196 (1986); Pontecorvo, G., Somatic Cell Gener. 1:397–400 (1975); Sharo, J., et al., Proc. Natl. Acad. Sci. USA 7:6:1420–1424 (1979); Shulman, M. et al., Nature 276:269–270 (1978); Springer, T. A. (ed), Hybridoma Technology in the Biosciences and Medicine, Plenum Press, New York, 1985; and Taggart, R. T. et al., Science 219:1228–1230 (1982)).

The mAbs of the present invention may be produced in large quantities by injecting hybridoma cells secreting the antibody into the peritoneal cavity of mice and, after appropriate time, harvesting the ascites fluid which contains a high titer of the mAb, and isolating the mAb therefrom. Alternatively, the mAbs may be produced by culturing hybridoma cells in vitro and isolating the secreted mAb from the cell culture medium.

Human genes which encode the C regions of the chimeric antibodies of the present invention are derived from cells which express, and preferably, produce, human immunoglobulins. The human $C_H$ region can be derived from any of the known classes or isotypes of human H chains, including gamma, μ, α, δ or ϵ. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), and μ (IgM).

The human $C_L$ region can be derived from either human L chain isotype, kappa or lambda.

Genes encoding human immunoglobulin C regions are obtained from human cells by standard cloning techniques (Sambrook, J. et al., Molecular Cloning: A Laboratory Manual, 2nd Edition, Cold Spring Harbor Press, Cold Spring Harbor, N.Y. (1989)). Human C region genes are readily available from known clones containing genes representing the two classes of L chains and the five classes of H chains. Chimeric antibody fragments, such as $F(ab')_2$ and Fab, can be prepared by designing a chimeric H chain gene which is appropriately truncated. For example, a chimeric gene encoding the H chain portion of an $F(ab')_2$ fragment would include DNA sequences encoding the $CH_1$ domain and hinge region of the H chain, followed by a translational stop codon to yield the truncated molecule.

Generally, the chimeric antibodies of the present invention are produced by cloning DNA segments encoding the H and L chain antigen-binding regions of a CCAA-specific antibody, preferably non-human, most preferably 33.28 or 31.1, and joining these DNA segments to DNA segments encoding human $C_H$ and $C_L$regions to produce chimeric immunoglobulin-encoding genes.

Thus, in a preferred embodiment, a fused gene is created which comprises a first DNA segment that encodes at least the antigen-binding region of non-human origin, such as a functionally rearranged V region with joining (J) segment, linked to a second DNA segment encoding at least a part of a human C region. This fusion can be accomplished by the polymerase chain reaction, as reported by Fernando et al., Miami Symp. Short Reports 3: 88, 1993.

The DNA encoding the antibody-binding region may be genomic DNA or cDNA. A convenient alternative to the use of chromosomal gene fragments as the source of DNA encoding the murine V region antigen-binding segment is the use of cDNA for the construction of chimeric immunoglobulin genes, as reported by Liu et al., Proc. Natl. Acad. Sci., USA 84:3439 (1987) and J. Immunology 139:3521 (1987), which references are hereby incorporated by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA-splicing systems.

Therefore, in an embodiment utilizing cDNA encoding the antibody V region, the method of producing the chimeric antibody involves several steps, outlined below:

1. Isolation of messenger RNA (mRNA) from the cell line producing the monoclonal antibody, cloning and cDNA production therefrom;
2. Preparation of a full length cDNA library from purified mRNA from which the appropriate V region gene segments of the L and H chain genes can be: (i) identified with appropriate probes, (ii) sequenced, and (iii) made compatible with a C gene segment;
3. Preparation of C region gene segments by cDNA preparation and cloning;
4. Construction of complete H or L chain coding sequences by linkage of the cloned specific V region gene segments to cloned human C region gene, as described above;
5. Expression and production of chimeric L and H chains in selected hosts, including prokaryotic and eukaryotic cells.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions may be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region ($C_{gamma\text{-}1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{gamma\text{-}1}$ region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric mouse-human antibody will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human $C_H$ region; polyadenylation and transcription termination occur at native chromosomal sites downstream of the human coding regions.

Gene expression elements useful for the expression of cDNA genes include: (a) viral transcription promoters and their enhancer elements, such as the SV40 early promoter (Okayama, H. et al., Mol. Cell. Biol. 3:280 (1983)), Rous sarcoma virus LTR (Gorman, C. et al., Proc. Natl. Acad. Sci., USA 79:6777 (1982)), and Moloney murine leukemia virus LTR (Grosschedl, R. et al., Cell 41:885 (1985)); (b) splice regions and polyadenylation sites such as those derived from the SV40 late region (Okayama et al., supra); and (c) polyadenylation sites such as in SV40 (Okayama et al., supra).

Immunoglobulin cDNA genes may be expressed as described by Liu et al., Supra, and Weidle et al., Gene 51:21 (1987), using as expression elements the SV40 early promoter and its enhancer, the mouse immunoglobulin H chain promoter enhancers, SV40 late region mRNA splicing, rabbit β-globin intervening sequence, immunoglobulin and rabbit β-globin polyadenylation sites, and SV40 polyadenylation elements. For immunoglobulin genes comprised of part cDNA, part genomic DNA (Whittle et al., Protein Engineering 1:499 (1987)), the transcriptional promoter may be human cytomegalovirus (CMV), the promoter enchancers derived from CMV and mouse/human immunoglobulin, and mRNA splicing and polyadenylation regions derived from the native chromosomal immunoglobulin sequences.

In one embodiment, for expression of cDNA genes in rodent cells, the transcriptional promoter is a viral LTR sequence, the transcriptional promoter enchancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with a chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture. In one embodiment, the fused genes encoding the chimeric H and L chains, or portions thereof, are assembled in separate expression vectors that are then used to co-transfect a recipient cell.

Each vector may contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. Subsequently, the genes so produced and amplified in a bacterial host are subsequently used to co-transfect a eukaryotic cell, and allow selection of a co-transfected cell carrying the desired transfected genes.

Examples of selectable genes of use in a bacterial system are the gene that confers resistance to ampicillin and the gene that confers resistance to chloramphenicol. Preferred selectable genes for use in eukaryotic transfectants include the xanthine guanine phosphoribosyl transferase gene (designated gpt) and the phosphotransferase gene from Tn5 (designated neo). Selection of cells expressing gpt is based on the fact that the enzyme encoded by this gene utilizes xanthine as a substrate for purine, nucleotide synthesis, whereas the analogous endogenous enzyme cannot. In a medium containing (1) mycophenolic acid, which blocks the conversion of inosine monophosphate to xanthine monophosphate, and (2) xanthine, only cells expressing the E gene can survive. The product of the neo blocks the inhibition of protein synthesis by the antibiotic G418 and other antibiotics of the neomycin class.

The two selection procedures can be used simultaneously or sequentially to select for the expression of immunoglobulin chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors.

Alternatively, the fused genes encoding the chimeric H and L chains can be assembled on the same expression vector.

For transfection of the expression vectors and production of the chimeric antibody, the preferred recipient cell line is a myeloma cell. Myeloma cells can synthesize, assemble and secrete immunoglobulins encoded by transfected immunoglobulin genes and possess the mechanism or glycosylation of the immunoglobulin. A particularly preferred recipient cell is the Ig-non-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric antibody construct of the present invention may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment (Johnston et al., Science 240:1538 (1988)). A preferred way of introducing DNA into lymphoid cells is by electroporation (Potter et al., Proc. Natl. Acad. Sci. USA 81:7161 (1984); Yoshikawa, K. et al., Jpn. J. Cancer Res. 77:1122–1133). In this procedure, recipient cells are subjected to an electric pulse in the presence of the DNA to be incorporated. Typically, after transfection, cells are allowed to recover in complete medium for about 24 hours, and are then seeded in 96-well culture plates in the presence of the selective medium. G418 selection is performed using about 0.4 to 0.8 mg/ml G418. Mycophenolic acid selection utilizes about 6 μg/ml plus about 0.25 mg/ml xanthine. The electroporation technique is expected to yield transfection frequencies of about $10^{-5}$ to about $10^{-4}$ for Sp2/0 cells. In the protoplast fusion method, lysozyme is used to strip cell walls from catarrhal harboring the recombinant plasmid containing the chimeric antibody gene. The resulting spheroplasts are fused with myeloma cells with polyethylene glycol.

The chimeric immunoglobulin genes of the present invention can also be expressed in nonlymphoid mammalian cells or in other eukaryotic cells, such as yeast, or in prokaryotic cells, in particular bacteria.

Yeast provides substantial advantages for the production of immunoglobulin H and L chains. Yeasts carry out posttranslational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides) (Hitzman, et al., 11th International Conference on Yeast, Genetics and Molecular Biology, Montpelier, France, Sep. 13–17, 1982).

Yeast gene expression systems can be routinely evaluated for the levels of production, secretion and the stability of chimeric H and L chain proteins and assembled chimeric antibodies. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promotor and terminator signals of the phosphoglycerate kinase (PGK) gene can be utilized. A number of approaches may be taken for evaluating optimal expression plasmids for the expression of cloned immunoglobulin cDNAs in yeast (see Glover, D. M., ed., DNA Cloning, Vol. II, pp. 45–66, IRL Press, 1985).

Bacterial strains may also be utilized as hosts for the production of antibody molecules or antibody fragments described by this invention. E. coli K12 strains such as E. coli W3110 (ATCC 27325), and other enterobacteria such as Salmonella typhimurium or Serratia marcescens, and various Pseudomonas species may be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches may be taken for evaluating the expression plasmids for the production of chimeric antibodies or antibody chains encoded by the cloned immunoglobulin cDNAs in bacteria (see Glover, D. M., ed., DNA Cloning, Vol. I, IRL Press, 1985).

Other preferred hosts are mammalian cells, grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which may be useful as hosts for the production of antibody proteins, in addition to the cells of lymphoid origin described above, include cells of fibroblast origin, such as Vero (ATCC CRL 81) or CHO-K1 (ATCC CRL 61).

Many vector systems are available for the expression of cloned H and L chain genes in mammalian cells (see Glover, D. M., ed., DNA Cloning, Vol. II, pp. 143–238, IRL Press, 1985). Different approaches can be followed to obtain complete $H_2L_2$antibodies. As discussed above, it is possible to co-express H and L chains in the same cells to achieve intracellular association and linkage of H and L chains into complete tetrameric $H_2L_2$ antibodies. The co-expression can occur by using either the same or different plasmids in the same host. Genes for both H and L chains can be placed into the same plasmid, which is then transfected into cells, thereby selecting directly for cells that express both chains. Alternatively, cells may be transfected first with a plasmid encoding one chain, for example the L chain, followed by transfection of the resulting cell line with an H chain plasmid containing a second selectable marker. Cell lines producing $H_2L_2$ molecules via either route could be transfected with plasmids encoding additional copies of H, L, or H plus L chains in conjunction with additional selectable markers to generate cell lines with enhanced properties, such as higher production of assembled $H_2L_2$ antibody molecules or enchanced stability of the transfected cell lines.

In addition to mAbs or chimeric antibodies, the present invention is also directed to an anti-idiotypic (anti-Id) antibody specific for V region epitopes of the mAb antibody or chimeric antibody of the invention. An anti-Id antibody is an antibody which recognizes unique determinants generally associated with the antigen-binding region of another antibody. The antibody specific for CCAA, such as 33.28, is termed the idiotypic or Id antibody. The anti-Id can be prepared by immunizing an animal of the same species and genetic type mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody. The anti-anti-Id may be epitopically Identical to the original antibody which induced the anti-Id. Thus, by using antibodies to the idiotypic determinants of a mAb, it is possible to identify other clones expressing antibodies of identical specificity.

Accordingly, the mAbs or chimeric antibodies of the present invention may be used to induce anti-Id antibodies in suitable animals, such as BALB/c mice. Spleen cells from such immunized mice can be used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a CCAA epitope.

The antibodies of the present invention, including their antigen-binding fragments and derivatives, have a multitude of uses relating to the diagnosis, monitoring and therapy of colon, breast, and ovarian cancer. Such uses are summarized in Schlom, J., Canc. Res., 46:3225–3238 (1986), which is hereby incorporated by reference.

In diagnosis, the antibodies may be used in immunoassays (described below) to screen body fluids, such as serum, sputum, effusions, urine, cerebrospinal fluid, and the like, for the presence of CCAA. The antibodies may be used for scanning or radioimaging, when labelled with an appropriate radiolabel, to detect primary or metastatic foci of tumor cells. Furthermore, the antibodies are useful in lymphoscintigraphy to detect lymph node involvement in the disease.

The antibodies of the present invention are also useful for immunopathological analysis, such as the differential diagnosis of tumor type, the subclassification of the tumor based on its expression of CCAA. Such determinations would be important in assessment of metastatic potential, predicted responses to therapy and prognosis.

In particular, because of the specificity of the mAbs and chimeric antibodies of the present invention, they may permit the definition of defining subpopulations of tumor cells among the heterogeneous cells present in a growing tumor. These antibodies could therefore be used in the typing and cross-matching of the tumor cell "lines" comprising the tumor by means of flow cytometry, both at the time of surgery and prior to therapy. An analysis of the tumor cell subpopulations with the antibodies of this invention, and a battery of additional mAbs, is used to define (a) which antigen preparation would be the most appropriate for specific active immunotherapy, (b) which mAb or chimeric antibody would be efficacious for ADCC, and (c) which antibody or combination of mAbs should be used for imaging the patient at a later date in search for recurrent or metastatic tumors.

In addition to their diagnostic utility, the antibodies of the present invention are useful for monitoring the progression of disease by screening body fluids for CCAA, radioimaging of tumor, or the detection of occult metastasis through aspiration cytology, lymph node or bone marrow biopsy, or cytology of body fluids.

A summary of the ways in which the antibodies of the present invention may be used therapeutically includes direct cytotoxicity by the antibody, either mediated by complement (CDC) or by effector cells (ADCC), conjugated to anti-tumor drugs, toxins, radionuclides. The antibodies can be used for ex vivo removal of tumor cells from the circulation or from bone marrow.

Some of these approaches are described in more detail below. Armed with the teachings provided herein, one of ordinary skill in the art will know how to use the antibodies of the present invention for diagnostic, monitoring or therapeutic purposes without undue experimentation.

The preferred animal subject of the present invention is a mammal. By the term "mammal" is meant an individual belonging to the class Mammalia. The invention is particularly useful in the treatment of human subjects.

By the term "treating" is intended the administering to subjects of the antibodies of the present invention or a fragment or derivative thereof for purposes which may include prevention, amelioration, or cure of colon, breast, and ovarian cancer.

The pharmaceutical compositions of the present invention may be administered by any means that achieve their intended purpose. Amounts and regimens for the administration of antibodies, their fragments or derivatives can be determined readily by those with ordinary skill in the clinical art of treating colon, breast, and ovarian cancer and related disease.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 ng/kg body weight to about 100 10 mg/kg body weight. The preferred dosages comprise 0.1 to 10 mg/kg body weight.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations, contain from about 0.01 to 99 percent, preferably from about 20 to 75 percent of active compound(s), together with the excipient.

Preparations of the antibody, fragment or derivative of the present invention for parenteral administration, such as in detectably labelled form for imaging or in a free or conjugated form for therapy, include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. See, generally, Remington's Pharmaceutical Science, 16th ed., Mack Publishing Co., Easton, Pa., 1980.

In particular, the antibodies, fragments and derivatives of the present invention are useful for treating a subject having or developing colon, breast, and ovarian adenocarcinoma. Such treatment comprises parenterally administering a single or multiple doses of the antibody, fragment or derivative, or a conjugate thereof.

The antibodies of this invention can be adapted for therapeutic efficacy by virtue of their ability to mediate ADCC and/or CDC against cells having CCAA associated with their surface. For these activities, either an endogenous source or an exogenous source of effector cells (for ADCC) or complement components (for CDC) can be utilized.

The antibodies of this invention, their fragments, and derivatives can be used therapeutically as immunoconjugates (see for review: Dillman, R. O., Ann. Int. Med. 111:592–603 (1989)). They can be coupled to cytotoxic proteins, including, but not limited to, Ricin-A, Pseudomonas toxin. Diphtheria toxin, and tumor necrosis factor. Toxins conjugated to antibodies or other ligands are known in the art (see, for example, Olsnes, S. et al., Immunol. Today 10:291–295 (1989)). Plant and bacterial toxins typically kill cells by disrupting the protein synthetic machinery.

The antibodies of this invention can be conjugated to additional types of therapeutic moieties including, but not limited to, diagnostic radionuclides and cytotoxic agents such as cytotoxic radionuclides, drug and proteins. Examples of radionuclides which can be coupled to antibodies and delivered in vivo to sites of antigen include $212_{Bi}$, $131_{I}$, $186_{Re}$, and $90_{Y}$, which list is not intended to be exhaustive. The radionuclides exert their cytotoxic effect by locally irradiating the cells, leading to various intracellular lesions, as is known in the art of radiotherapy.

Cytotoxic drugs which can be conjugated to antibodies and subsequently used for in vivo therapy include, but are not limited to, daunorubicin, doxorubicin, methotrexate, and Mitomycin C. Cytotoxic drugs interface with critical cellular processes including DNA, RNA, and protein synthesis. For a fuller exposition of these classes of drugs which are known in the art, and their mechanisms of action, see Goodman, A. G., et al., Goodman and Gilman's THE PHARMACOLOGICAL BASIS OF THERAPEUTICS, 7th Ed., Macmillan Publishing Co., 1985.

The antibodies of this invention may be advantageously utilized in coordination with other monoclonal or chimeric antibodies, or with lymphokines or hemopoietic growth factors, etc., which serve to increase tee number or activity of effector cells which interact with the antibodies.

The antibodies, fragments, or derivatives of this invention, attached to a solid support, can be used to remove soluble colon carcinoma-associated antigens from fluids or tissue or cell extracts. In a preferred embodiment, they are used to remove soluble tumor antigens from blood or blood plasma products. In another preferred embodiment, the antibodies are advantageously used in extracorporeal immunoadsorbent devices, which are known in the art (see, for example, Seminars in Hematology, Vol. 26 (2 Suppl. 1) (1989)). Patient blood or other body fluid is exposed to the attached antibody, resulting in partial or complete removal of circulating CCAA (free or in immune complexes), of CCAA-bearing cells, following which the fluid is returned to the body. This immunoadsorption can be implemented in a continuous flow arrangement, with or without interposing a cell centrifugation step. See, for example, Terman, D. S. et al., J. Immunol. 117:1971–1975 (1976).

The present invention also provides the above antibodies, fragments and derivatives, detectably labelled, as described below.

The antibodies of the present invention are useful for immunoassays which detect or quantitate CCAA or cells bearing CCAA in a sample. Such an immunoassay typically comprises incubating a biological sample in the presence of a detectably labelled antibody of the present invention capable of identifying the tumor antigen, and detecting the labelled antibody which is bound in a sample.

Thus, in this aspect of the invention, a biological sample may be treated with nitrocellulose, or other solid support or carrier which is capable of immobilizing cells, cell particles or soluble proteins or glycoproteins. The support may then be washed with suitable buffers followed by treatment with the detectably labelled antibody of the present invention. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers include glass, polystyrene, polypropylene, polyethylene, dextran, nylon, amylases, natural and modified celluloses, polyacrylamides, agaroses, and magnetic. The nature of the carrier can be either soluble to some extent or insoluble for the purposes of the present invention. The support material may have virtually any possible structural configuration so long as the coupled molecule is capable of binding to CCAA or the antibody specific for CCAA. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of antibody may be determined according to well-known methods. Those skilled in the art will be able to determine operative and optimal assay conditions for each determination by employing routine experimentation.

One of the ways in which the antibody of the present invention can be detectably labelled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner may be an antibody against the constant or variable region of the antibody of the invention, such as a heterologous anti-mouse immunoglobulin antibody. Alternatively, the binding partner may be a non-antibody protein capable of binding to the antibody of the present invention, such as staphylococcal protein A, or streptococcal protein G.

Enzymes which can be used to detectably label the CCAA-specific antibodies of the present invention, or the binding partners for these antibodies, include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glycoamylase and acetylcholinesterase.

By radioactively labelling the antibody of the present invention or the binding partner, it is possible to detect CCAA through the use of a radioimmunoassay (RIA) (see, for example, Work, T. S. et al., Laboratory Techniques and Biochemistry in Molecular Biolog. North Holland Publishing Company, N.Y. (1978)). The radioactive isotope can be detected by such means as the use of a gamma counter or a scintillation counter or by autoradiography. Isotopes which are particularly useful for the purpose of the present invention are well known in the art.

It is also possible to label the antibodies or binding partners with a fluorescent compound. When the fluorescently labelled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and flourescamine.

The antibodies can also be detectably labelled using fluorescence-emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibodies of the present invention also can be detectably labelled by coupling to a chemiluminescent compound. The presence of the chemiluminescently labelled antibody is then determined by detecting the presence of luminescence that arises during the course of a chemical reaction. Examples of particularly useful chemiluminescent labelling compounds are luminol, isoluminol, imidazole, acridinium salt and oxalate ester.

Likewise, a bioluminescent compound may be used to label the antibody, fragment or derivative of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labelling are luciferin, luciferase and sequorin.

Detection of the antibody, fragment or derivative may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

In situ detection may be accomplished by removing a histological specimen from a patient, and providing the labelled antibody, or the unlabelled antibody plus a labelled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In a preferred embodiment, an avidin-biotin immunoperoxidase staining system can be used, and a kit utilizing this system is also contemplated.

The kit employing mAbs or chimeric antibodies of the present invention can be used for immunohistochemical evaluation of colon, breast, and ovarian carcinoma. Indications for tissue study are to evaluate subpopulations of tumor cells that express the antigens defined by mAbs 31.1 and 33.28.

The colon kit is comprised of the reagents necessary for immunohistochemical analysis as follows:

a) mAbs 31.1, 33.28 or mouse/human chimeric antibody Chi #1, and the mAb for carcinoembryonic antigen (CEA), the latter representing the standard monoclonal used for colon tissue immunohistochemistry;

b) reagents for immunoperoxidase (blocking reagent) in the form of, for example, goat serum; and secondary antibody, such as, for example, goat anti-mouse antibody;

c) immunoperoxidase; and d) reagents to produce the brown coloration.

Similar kits can be employed for the immunohistochemical analysis of breast and ovarian carcinoma.

The immunoperoxidase technique to be employed is that of Sternberger. The primary antibody (mAb or chimeric antibody) serves as an antigen which can bind more than one secondary antibody. The secondary antibodies form a "bridge" between the primary antibody and the horseradish peroxidase-antiperoxidase complexes.

The kit contemplated herein can be used to study fully developed colon, carcinoma, polyps in transformation to define the extent of malignant transformation, benign polyps to see if a site of transformation has been missed and inflammatory bowel disease to evaluate any sites of undetected transformation. Similar kits can be employed to study breast and ovarian carcinomas.

Another kit similar to the above kit is also contemplated which uses all five mAbs to colon carcinoma in order to evaluate all subpopulations of tumors and as such has the capability to type and cross-match the lesions.

The antibody, fragment or derivative of the present invention may be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labelled soluble antibody is added to permit detection and/or quantitation of the ternary complex formed between solid-phase antibody, antigen, and labelled antibody.

Typical, and preferred, immunometric assays include "forward" assays in which the antibody bound to the solid phase is first contacted with the sample being tested to extract the tumor antigen from the sample by formation of a binary solid phase antibody-CCAA complex. After a suitable incubation period, the solid support is washed to remove the residue of the fluid sample, including unreacted tumor antigen, if any, and then contacted with the solution containing an unknown quantity of labelled antibody (which functions as a "reporter molecule"). After a second incubation period to permit the labelled antibody to complex with the CCAA bound to the solid support through the unlabelled antibody, the solid support is washed a second time to remove the unreacted labelled antibody. This type of forward sandwich assay may be a simple "yes/no" assay to determine whether CCAA is present or may be made quantitative by comparing the measure of labelled antibody with that obtained for a standard sample containing known quantities of the antigen. Such "two-site" or "sandwich" assays are described by Wide (Radioimmune Assay Method, Kirkham, ed., E. & S. Livingstone, Edinburgh, 1970, pp. 199–206).

Other type of "sandwich" assays, which may also be useful with CCAA, are the so-called "simultaneous" and "reverse" assays. A simultaneous assay involves a single incubation step wherein the antibody bound to the solid support and labelled antibody are both added to the sample being tested at the same time. After the incubation is completed, the solid support is washed to remove the residue of fluid sample and uncomplexed labelled antibody. The presence of labelled antibody associated with the solid support is then determined as it would be in a conventional "forward" sandwich assay.

In the "reverse" assay, stepwise addition first of a solution of labelled antibody to the fluid sample, followed by the addition of unlabelled antibody bound to a solid support after a suitable incubation period, is utilized. After a second incubation, the solid phase is washed in conventional fashion to free it of the residue of the sample being tested and the solution of unreacted labelled antibody. The determination of labelled antibody associated with a solid support is then determined as in the "simultaneous" and "forward" assays. In one embodiment, a combination of antibodies of the present invention specific for separate epitopes may be used to construct a sensitive three-site immunoradiometric assay.

For purposes of in vivo imaging of colon, breast, and ovarian cancer using the antibodies of the present invention, there are many different labels and methods of labelling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the antibodies used in the invention, or will be able to ascertain such, using routine experiments. Furthermore, the binding of these labels to the antibody can be done using standard techniques common to those of ordinary skill in the art.

For diagnostic in vivo imaging, the type of detection instrument available is a major factor in selecting a given radionuclide. The radionuclide chosen must have a type of decay which is detectable by a given type of instrument. In general, any conventional method for visualizing diagnostic imaging can be utilized in accordance with this invention.

Another important factor in selecting a diagnostic radionuclide for in vivo imaging is that the half-life of a radionuclide be long enough so that it is still detectable at the time of maximum uptake by the target issue, but short enough so that deleterious radiation of the host is minimized. In one preferred embodiment, a radionuclide used for in vivo imaging does not emit particles, but produces a large number of photons in a 140–200 keV range, which may be readily detected by conventional gamma cameras.

For in vivo diagnosis, radionuclides may be bound to the antibody either directly or indirectly by using an intermediary functional group. Intermediary functional groups which are often used to bind radioisotopes which exist as metallic ions to the antibodies are the chelating agents, diethylene triamine pentaacetic acid (DTFA) and ethylene diamine tetraacetic acid (EDTA). Examples of metallic ions which can be bound to the antibodies of the present invention are $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$TI.

The specifically exemplified mAbs 33.28 and 31.1, and the chimeric antibody Chi #1 may be used to facilitate the production of additional mAbs which bind the same or immunologically cross-reactive colon carcinoma-associated antigens. First, these antibodies may be conjugated to a chromatographic support, and used to immunopurify colon carcinoma-associated antigens. These purified antigens, in turn, may be used to stimulate an immune response in suitable animals. Secondly, spleen cells from the responsive animals may be fused to immortalizing cells, and the resulting hybridomas screened for secretion of antibodies which bind to the purified antigen and/or whose binding to colon carcinoma-associated antigen is competitively inhibited by antibody 33.28 or 31.1, or chimeric antibody Chi #1.

Having now generally described the invention, the same will be further understood by reference to certain specific examples which are included herein for purposes of illustration only and are not intended to be limiting unless otherwise specified.

EXAMPLE I

Preparation and Characterization of the Colon Carcinoma-Associated Antigen (CCAA)

The antigenic preparation was obtained from pooled colon carcinoma membranes according to the method described by Hollinshead et al., Cancer 56:480 (1985). This antigenic material was purified to the extend that the membrane fractions were free of HL-A antigens and were separated from much of the non-immunogenic glycoprotein fractions. In its final form the antigenic preparation was shown to be immunogenic in a specific manner in humans as evidenced by its capability of eliciting a delayed hypersensitivity reaction only in patients with active colon, breast, and ovary carcinoma.

Tumor cell suspensions in saline were prepared from fresh operating room specimens. Single cell suspensions, obtained by conventional means, were centrifuged for 10 minutes at about 400×g and the supernatant was retained. The cell pellet was resuspended and recentrifuged. The membrane material was examined by electron microscopy to assure that only membrane material (and no intact cells) was present, and the protein content was measured by the Lowry method.

The membrane material was next subjected to sequential low frequency sonication and resuspended as a soluble pool of membrane proteins. The soluble sonicates were separated by gel filtration on Sephadex-6200. Fractions of 2 ml were collected and the absorbance profile at 220 and 280 μm was recorded. Fractions comprising individual protein peaks were pooled, and the pools were concentrated by Diaflo ultrafiltration. Sephadex-G200 fractions IB and IIA, as defined by Hollinshead et al., (supra), were further purified by gradient polyacrylamide gel electrophoresis (PAGE). The fractions were tested for their ability to elicit positive delayed cutaneous hypersensitivity reactions in patients with colon carcinoma. Those fractions with immunogenic activity were said to contain colon carcinoma-associated antigens (CCAA) and were employed as immunogens and screening agents in the preparation of the mAbs.

By gradient PAGE, a double-banded antigen distinct from that of carcinoembryonic antigen (Gold, P. et al., J. Exp. Med. 122:467–481 (1965); Hollinshead, A. et al., Cancer 56:480 (1985)) was identified and isolated. The bands comprising this antigen migrated 6.3 and 6.6 cm. distant from tracking dye. Biochemical analysis of the antigen proved that it was glycoprotein. The molecular weight of the antigen was estimated based on the electrophoretic mobility of transferrin (6.4–6.5 cm) which has a molecular weight of 76.5 kDa.

EXAMPLE II

Preparation and Screening of Monoclonal Antibodies

Monoclonal antibodies (mAbs) against human colon carcinoma-associated antigens (CCAA) were obtained by the production and cloning of hybrids resulting from the fusion of mouse myeloma cells Sp2/0-Ag14 with spleen cells from BALB/c mice which had been immunized with the CCAA described above.

Five hybrid clones were established, as described below, and designated as 31.2, 31.1, 77, 33.23 and 33.28. All five mAbs reacted strongly with the CCAA and with two colon carcinoma cell lines (SW480 and SW620) when assayed by ELISA. Two of the mAbs, 31.1. and 33.28, were studied in greatest detail.

A. Immunization and Cell Fusion

BALB/c mice were immunized by intrapertioneal injection of 50 μg of the CCAA described above emulsified in complete Freud's adjuvant, as described by Hollinshead in clinical trials (Hollinshead et al., supra). Ten days later the mice received an intravenous booster injection of the same amount of CCAA in saline. Mice were sacrificed three days later and their spleen cells obtained. Cell fusion was performed by incubation $5\times10^7$ mouse spleen cells with $10^7$ sP2/0-Ag14 myeloma cells in 40% polyethylene glycol (MW=1500)

B. Screening of Hybrid Clones

An enzyme-linked immunosorbent assay (ELISA), described by Tsang et al., JNCI77:1175 (1986), was used for the detection of hybridoma clones producing antibodies specific for the CCAA. CCAA (100 n/well) was immobilized on polystyrene microplates. Antibodies present in the test supernatants were allowed to bind to the immobilized antigen. The presence of the bound murine mAbs was detected with peroxidase-conjugated second antibodies, specific for mouse immunoglobulins, followed by the chromogenic substrate for peroxidase, O-phenyldiamine. Wells showing color reactions yielding Absorbances ≧0.500 units were scored as positive. Negative controls gave values of 0.01 to 0.09 units.

Hybridoma wells scoring as positive by ELISA were further screened by indirect immunofluorescene, using various tumor cells and normal cells as identified in Table 1, below. All of the tumor cell lines were obtained from the ATCC. Cells were incubated with hybridoma culture supernatants at an appropriate dilution (1:2) in phosphate buffered saline (PBS) for 1 hour at 4° C. The cells were washed and incubated with a fluorescein-labelled goat anti-mouse immunoglobulin antibody. The cells were then washed three times with PBS and examined by fluorescence microscopy. The results appear in Table 1.

TABLE 1

INDIRECT IMMUNOFLUORESCENCE REACTIVITY OF ANTI-COLON CARCINOMA-ASSOCIATED ANTIGEN(S) (COAA) MoAbS WITH HUMAN CULTURE CELLS[A]

| CELLS | REACTIVITY OF MoAbS[B] | | | | |
|---|---|---|---|---|---|
| | 31.2 | 77 | 31.1 | 33.28 | 33.23 |
| TUMOR LINES | | | | | |
| SW948 (COL) | − | + | − | − | − |
| HCT116 (COL) | − | − | − | + | − |
| WIDR (COL) | + | + | + | + | + |
| COLO320 (COL) | + | + | + | − | − |
| HS619 (COL) | − | − | − | − | − |
| HS853 (COL) | − | − | − | − | − |
| CACO-2 (COL) | + | + | − | − | − |
| SK-CO-1 (COL) | + | + | − | + | + |
| HT-29 (COL) | + | + | − | + | + |
| SW1116 (COL) | + | − | − | + | + |
| SW480 (COL) | + | + | + | + | + |
| SW620 (COL) | + | + | + | + | + |
| 231 (BE) | − | − | − | − | − |
| CAMA-1 (BE) | − | − | − | − | − |
| PAN-1 (PAN) | − | − | + | − | − |
| MIA (PAN) | − | − | + | − | − |
| HS766T (PAN) | − | − | − | − | − |
| M-14 (MEL) | − | − | − | − | − |
| HT1080 (FIB) | − | − | − | − | − |
| LM (OS) | − | − | − | − | − |
| TE-85 (OS) | − | − | − | − | − |
| NORMAL SKIN FIBROBLAST | − | − | − | − | − |
| BONE MARROW CELL | − | − | − | − | − |
| NORMAL HUMAN PBMC | − | − | − | − | − |

[A]CULTURE SUPERNATANT WAS DILUTED 1:2 WITH PBS.
[B]POSITIVE (+) AND NEGATIVE (−) REACTIVITIES WERE DEFINED BY INTENSITY OF THE MEMBRANE FLUORESCENCE AS COMPARED TO THE BACKGROUND.
C. COL: COLON CARCINOMA; BR: BREAST CARCINOMA; PAN: PANCREATIC CARCINOMA; FIB: FIBROSOMCOMA.

EXAMPLE III

Analysis of Monoclonal Antibodies and their Reactivity

The anti-CCAA mAbs produced and detected as above were also tested for reactivity with fresh human tissue. Cryostat sections of the tissue types listed in Table 2, below, were fixed with 3.5% formaldehyde in PBS and then washed three times with PBS. For indirect immunofluorescence studies, the sections were incubated with the mAbs and then stained with a fluorescein-labelled second antibody as above.

As is shown in Table 2, mAbs 31.1 and 33.28 were highly specific for colon carcinoma cells. This indicates that an antigen (CCAA) which was highly specific for colon carcinoma and, furthermore, was immunogenic in colon carcinoma patients (positive DH reactions), and served as a successful immunogen in mice for the devnd phycoerythrin excitation was used. Trigger regions were established by examining cells by forward versus 90° light scatter. As shown in Table 4, both 31.1 and 33.28 bound to colon carcinoma cells; neither mAb bound significantly to PBMC.

TABLE 2

Indirect Immunofluorescence of Anti-CCAA Mabs with Flesh Human Tissues[a]

| Tissues | Reactivity of Mabs | |
|---|---|---|
| | 33.28 | 31.1 |
| Tumor | | |
| Colon Carcinoma | 3/3 | 3/3 |
| Pancreatic Carcinoma | 0/2 | 0/2 |
| Melanoma | 0/2 | 0/1 |
| Breast Carcinoma | 0/2 | 0/1 |
| Normal | | |
| Placenta | 0/1 | 0/1 |
| Liver | 0/1 | 0/1 |
| Colon | 0/3 | 0/3 |
| Spleen | 0/1 | 0/1 |
| Thymus | 0/1 | 0/1 |
| Muscle | 0/1 | 0/1 |

[a]Ascitic fluid was diluted 1:50 with PBS. Cryostat sections (4–6 μM thick) were fixed with 3.5% formaldehyde in PBS for 10 minutes and then washed three times in PBS. Sections were stored at −70° C. unless used immediately. Results are expressed as number of positive/negative of tissue tested.

Table 3 shows the results of an immunoabsorption analysis of the Mabs. Three colon carcinoma cell lines (HT-29, WIDR and SW 620) and an osteosarcoma cell line (LM) were used to absorb fluorescein isothiocyanate (FITC)-conjugated Mabs 31.1 or 3.28. Ascites fluid from mice in which the hybridomas were growing, diluted 1:50, was added to the absorbing cells. The mixtures were incubated for 1 hr at 4° C. Either $2\times10^7$ cells (Table 3, Part A) or $10^4$ cells (Table 3, Part 5) were used to absorb the antibodies (Table 3) The osteosarcoma cell line did not absorb out 31.1 or 33.28 activity, while the colon carcinoma cell lines did.

TABLE 3

Immunoabsorption Analysis of mAbs

| mAb | Absorbing Cells | | | | | | | |
|---|---|---|---|---|---|---|---|---|
| | HT-29 | | WIDR | | SW620 | | LM | |
| | A | B | A | B | A | B | A | B |
| 33.28 | − | + | − | + | − | + | + | + |
| 31.1 | − | + | − | + | − | + | + | + |

Cytofluorometric analysis was used to measure the binding of 31.1. 33.28 and a control mAb to HT29, WIDR and SW480 tumor cells and to peripheral blood mononuclear cells (PBMCs) An Ortho Spectrum III Cytofluorograph, equipped with an argon laser capable of fluorescein and phycoerythrin excitation was used. Trigger regions were established by examining cells by forward versus 90° light scatter. As shown in Table 4, both 31.1 and 33.28 bound to colon carcinoma cells; neither mAb bound significantly to PBMC.

TABLE 4

SUMMARY OF CYTOFLUOROMETRIC ANALYSIS

| Cells | % of cells stained with mAb: 33.28 | 31.1 | Control |
|---|---|---|---|
| HT29 | 51.0 | 53.9 | 9.2 |
| WiDr | 21.0 | ND | 8.1 |
| SW480 | 37.0 | 32.0 | 3.8 |
| PBMC | 2.1 | 2.1 | ND |

The heavy and light chain isotypes of the mAbs were determined by immunodiffusion. The 31.1 mAb was found to be an IgG1 with a kappa light chain. The 33.28 mAb was found to be an IgG2a with a kappa light chain (Table 5). This is in strong contrast to the prior art mAb 19.9 (Herlyn, M. et al., J. Biol. Chem. 257:14365–14369 (1982)) which is of the IgG1 class (Herlyn, D. et al., Proc. Natl. Acad. Sci. USA 79:4761–4765 (1982)). Importantly, antibodies of the IgG2a class are expected to be more useful for immunotherapeutic purposes (Colcher, D. et al., Proc. Natl. Acad. Sci. USA 78:3199–3203 (1981)). Although the 19.9 mAb has reactivity to colon tumors, it was derived by immunization with pancreatic carcinoma antigens, and is therefore cross-reactive with colon. This is analogous to the situation with the B72.3 mAb ([citation]), which is a colon-reactive antibody obtained by immunization with breast cancer tissue.

TABLE 5

Isotyping of Monoclonal Antibodies

| Culture Supernatant | IgG1 | IgG2a | IgG2b | IgM | Light Chains Kappa | Lambda |
|---|---|---|---|---|---|---|
| 31.2 | − | + | − | − | + | − |
| 31.1 | + | − | − | − | + | − |
| 77 | − | − | + | − | + | − |
| 33.23 | − | + | − | − | + | − |
| 33.28 | − | + | − | − | + | − |

EXAMPLE IV

Characterization of the Colon Carcinoma-Associated Antigen

The molecular mass of the antigens to which the above mAbs bound was determined by Western blot analysis using soluble protein extracted from colon carcinoma cell lines SW480 and SW620. The 33.28 [and 31.1 mAbs] *antibody* reacted with molecules having *an* apparent molecular [weights] *weight* of 61.1 kDa[and 72 kDa, respectively], from both of these cells lines. [These mAbs] *The 33.28 and 31.1 mAbs* did not react with material from human PBMCs or from human tumor cell lines of other histologic types in Western blot analysis.

In order to define better the specificity of the mAbs of the present invention for the immunizing CCAA and to establish whether the mAbs reacted with an immunogenic component of the cell membrane preparation which has been used in clinical immunotherapy trials (Hollinshead et al., supra), the original immunogenic preparation described above was performed by high performance liquid chromatography (HPLC).

The analysis revealed 4 distinct peaks, each of which was tested for immune reactivity (elicitation of DH) in patients with colon carcinoma by skin test (FIG. 1). Among the 10 patients with colon carcinoma tested only the material in peak #4 induced a cutaneous DH reaction. The peak #4 antigen was found to react with mAb 33.28, while mAb 31.1 reacted with peak #3, the next most prominent peak.

The references cited above are all incorporated by reference herein.

EXAMPLE V

Affinity Purification of Colon Carcinoma-Associated Antigen

The mAb 33.28 was used in affinity chromatography to isolate antigen extracted from cells of the HT-29 line. Five mg of purified 33.28 IgG was coupled to CNBr-activated sepharose 4B. The column was pre-eluted with 0.05M diethylamine, pH 11.5, and then equilibrated with 0.14M NaCl/0.01M Tris (pH 8.0). CCAA preparation was applied to the column, and the column was eluted with 0.05M diethylamine, pH 11.5. The eluted fractions were neutralized by the addition of IM Tris-HCl, pH 8.0.

The material bound and eluted from the 33.28 affinity matrix was then subjected to HPLC. The eluted CCAA preparation was adjusted in starting buffer (0.01M sodium phosphate buffer, pH 7.0), applied to a Synchropak Wax weak anion exchange HPLC column (250×4.6 mm) and eluted with a gradient of 0 to 1M NaCl in 0.01M sodium phosphate buffer, pH 6.0, at a flow rate of 1 ml/min. Anion exchange chromatography was performed using a Hewlett-Packard HPLC (HP 1090, Hewlett-Packard, Arondale, Pa.).

Figure 2:
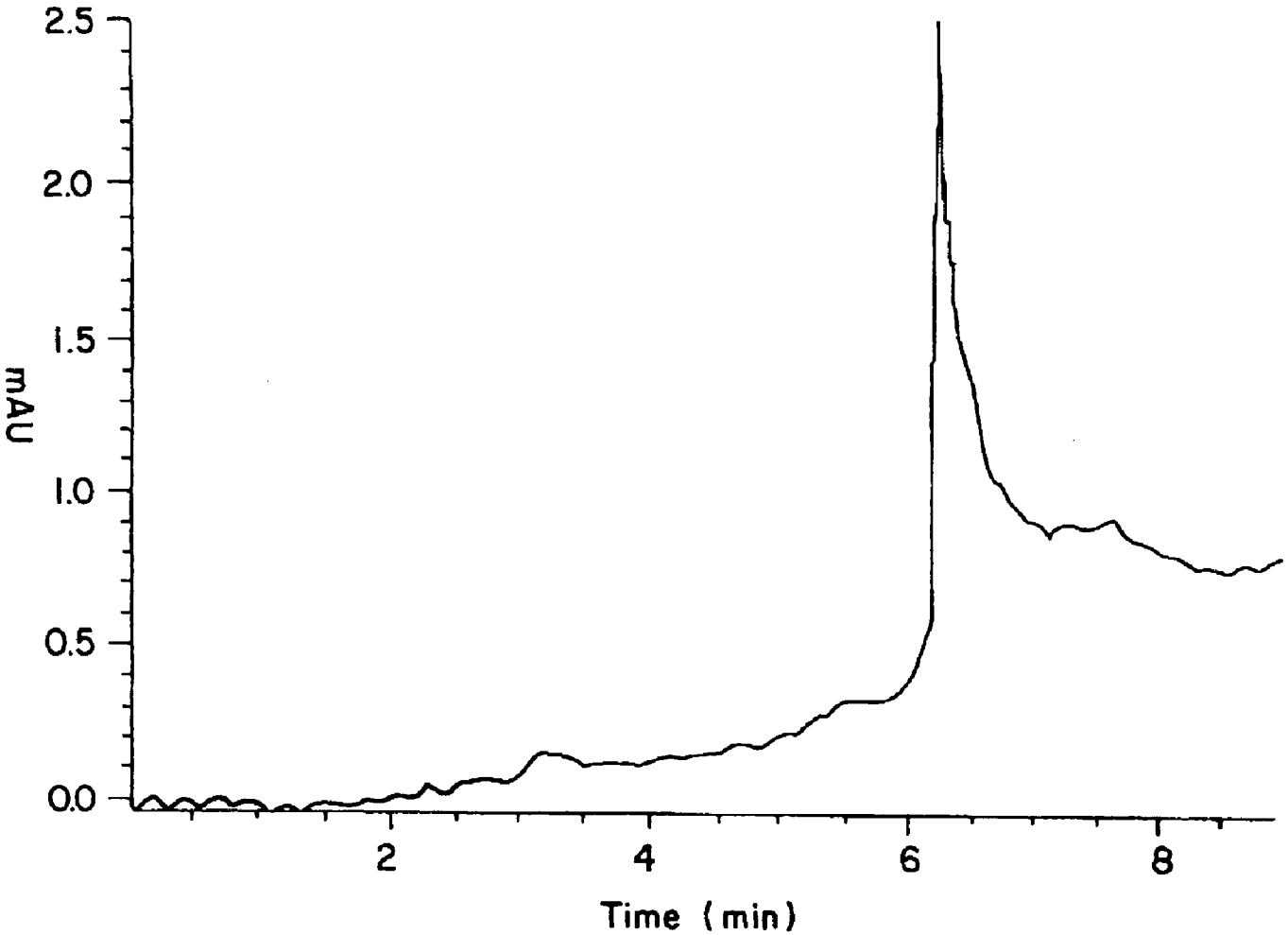
FIG. 2 is a tracing showing an HPLC elution profile of the colon carcinoma-associated antigen obtained by affinity purification of the material contained in peak 4 of FIG. 1.

Results appear in FIG. 2. The antigenic material derived from HT-29 cells isolated by mAb 33.28 gave a peak that matched peak #4 described above and had similar immunogenic activity in humans, indicating the utility of mAb 33.28 for isolation of a colon cancer preparation which is immunogenic for humans.

EXAMPLE VI

ADCC Activity of mAbs 33.28 and 31.1

In order to be therapeutically useful, a mAb specific for an immunogenic tumor antigen should have the following properties: (a) high tumor tissue specificity, (b) absence of cross-reactivity to normal human tissue, and (c) a biological activity associated with destruction of tumors, such as antibody-dependent cellular cytotoxicity (ADCC).

The ADCC activity of mAbs 33.28 and 31.1 was tested on the colon carcinoma line WiDR as target cell. The melanoma cell line, M-14, served as a specificity control. ADCC was assayed using a conventional 4 hr. $^{51}Cr$ release assay using normal human PBMC as effector cells, and the results are shown as percent isotope release (% lysis) (Table 6). The background lysis was 8.3%. At an effector:target ratio of 100:1, mAb 33.28 caused 40.3% lysis of tumor cells, and 31.1 induced 51.8% lysis.

TABLE 6

ADCC Activity of mAbs 33.28 and 31.1

| Antibody or Control | % Lysis of Target Cells at E:T Ratios: WiDR 25 | WiDR 50 | WiDR 100 | M-14 25 | M-14 50 | M-14 100 |
|---|---|---|---|---|---|---|
| 33.28 | 23.1 | 40.3 | 45.3 | 6.9 | 8.4 | 9.0 |
| 31.1 | 14.3 | 26.7 | 51.8 | 7.5 | 6.4 | 8.7 |
| OSA1 | 10.0 | 9.2 | 12.2 | 11.4 | 14.8 | 10.9 |
| NMS | 12.2 | 11.7 | 13.1 | 14.2 | 15.0 | 11.1 |
| PBS | 8.2 | 5.1 | 7.6 | 11.0 | 14.2 | 10.5 |

ADCC was assayed by a 4 hour $^{51}$Cr release assay. Background $^{51}$Cr release was 8.3%. E:T Ratio indicates effector cell-to-target ratios. The mAb or serum was tested at a 1:100 dilution; OSA1 - mAb to-osteosarcoma associated antigens; NMS - normal mouse serum; WiDr - colon carcinoma cell line; M14 - melanoma cell line.

EXAMPLE VII

Detection of Circulating CCAA with mAbs 33.28 and 31.1

The mAbs of the present invention were tested for their ability to detect circulating CCAA in 79 unknown serum samples (Table 7). The assay was based on the ability of the serum samples to inhibit binding of the mAb to the CCAA in ELISA. None of the 50 normal serum samples gave false positive results. Nine of the ten serum samples from patients with active colon carcinoma were positive. None of the sera from disease-free colon cancer patients one year post-resection were positive.

TABLE 7

Detection of Circulating Colon Carcinoma-Associated Antigen

| DONOR CONDITION | No. of Samples | No. of sera inhibiting binding of mAbs: 33.28 <15% (Neg) | 33.28 >15% (Pos) | 31.1 <15% (Neg) | 31.1 >15% (Pos) |
|---|---|---|---|---|---|
| Colon Carcinoma | 10 | 3 | 7 | 2 | 8 |
| Colon Carcinoma (Resected) | 4 | 4 | 0 | 4 | 0 |
| Breast Carcinoma | 9 | 9 | 0 | 9 | 0 |
| Melanoma | 5 | 5 | 0 | 5 | 0 |
| Prostate Cancer | 1 | 1 | 0 | 1 | 0 |
| Normal Serum | 50 | 50 | 0 | 50 | 0 |

Colon carcinoma-associated antigens was detected by ELISA. 100 μl of serum were used in each assay.

EXAMPLE VIII

Comparison of Specificity with Other mAbs Reactive with Colon Tumors

Further studies of tumor specificity were conducted using ELISA (Table 8). The mAb 31.1 was compared with CC49, a colorectal carcinoma-specific mAb purified from B-72.3, and a control mouse myeloma protein. 31.1 was shown to react with a narrower range of colorectal carcinomas than did CC49. However, it had a higher degree of specificity, having lower or no cross-reactivity with stomach tumors or normal colon tissue.

TABLE 8

ELISA ON NORMAL AND TUMOR TISSUES USING MAbs 31.1 CC49 AND MOPC-21

| Tissues | 31.1 | CC49 | MOPC-21 |
|---|---|---|---|
| Colorectal Carcinomas | | | |
| 1. COCA2A | – | +++ | – |
| 2. COCA2 | – | +++ | – |
| 3. COCA3 | + | ++ | – |
| 4. COCA4 | +++ | +++ | – |
| 5. G820 | ± | ++ | – |
| 6. G853 | +++ | ++ | – |
| 7. G817 | +++ | +++ | – |
| 8. G781 | – | – | – |
| Other Carcinomas | | | |
| 1. Breast CA1 | – | – | – |
| 2. Breast CA2 | – | – | – |
| 3. Lung CA1 | – | – | – |
| 4. Lung CA2 | – | – | – |
| 5. Ovarian CAD106 | – | – | – |
| 6. Ov CA5 | – | – | – |
| 7. Ov CAV5 | – | – | – |
| 8. Ov CAV45 | – | – | – |
| 9. Ov CAV43 | – | – | – |
| 10. Stomach CA14A | ++ | +++ | |
| 11. Stomach CA12A | – | +++ | – |
| 12. Stomach CA15A | – | – | – |
| Other Normal Tissues | | | |
| 1. Endometrium E21 | – | – | – |
| 2. Endometrium EC19 | – | – | – |
| 3. Endometrium EC17 | – | + | – |
| 4. Endometrium EC18 (RBC) | – | – | – |
| 5. Red blood cells 1 | – | – | – |
| 6. RBC 2 | – | – | – |
| 7. RBC 3 | – | – | – |
| 8. RBC 4 | – | – | – |
| 9. RBC 5 | – | – | – |
| 10. RBC 6 | – | – | – |
| 11. RBC 7 | – | – | – |
| 12. RBC 8 | – | – | – |
| 13. RBC 9 | – | – | – |
| 14. RBC 10 | – | – | – |
| 15. RBC 11 | – | – | – |
| 16. Granulocytes | – | – | – |
| 17. 385 | – | – | – |
| 18. 386 | – | – | – |
| 19. Normal spleen 3 | – | – | – |
| 20. 392 (N. Spleen) | – | – | – |
| 21. 395 (N. Liver) | – | – | – |
| 22. 387 (N. Kidney) | – | – | – |
| 23. 398 (N. Spleen) | – | – | – |
| 24. 390 (N. Liver) | – | – | – |
| 25. N. Spleen #1 | – | – | – |
| 26. N. Spleen #2 | – | – | – |
| 27. 800 (N. Colon) | – | ++ | – |
| 28. N. Colon (GW) | – | ++ | – |
| 29. N. Colon (Meloy) | – | – | – |
| 30. N. Colon | – | – | – |
| 31. G1155B (N. Colon) | – | – | – |
| 32. G1164B (N. Colon) | – | – | – |
| 33. N. Colon | ± | – | – |
| 34. Normal Stomach A | – | – | – |
| 35. N. Stomach B | – | – | – |
| 36. N. Stomach C | – | – | – |
| 37. Normal Lung | – | – | – |
| 38. Normal Liver | – | – | – |

CC49 - NCI monoclonal antibody to colorectal carcinomas
MOPC-21 - negative control myeloma protein
All monoclonal antibodies were used at 40 ng/well, POGAM at 1:3000 dilution

EXAMPLE IX

In Vivo Localization of mAbs 33 28 and 31.1 to Tumors

Figure 3:
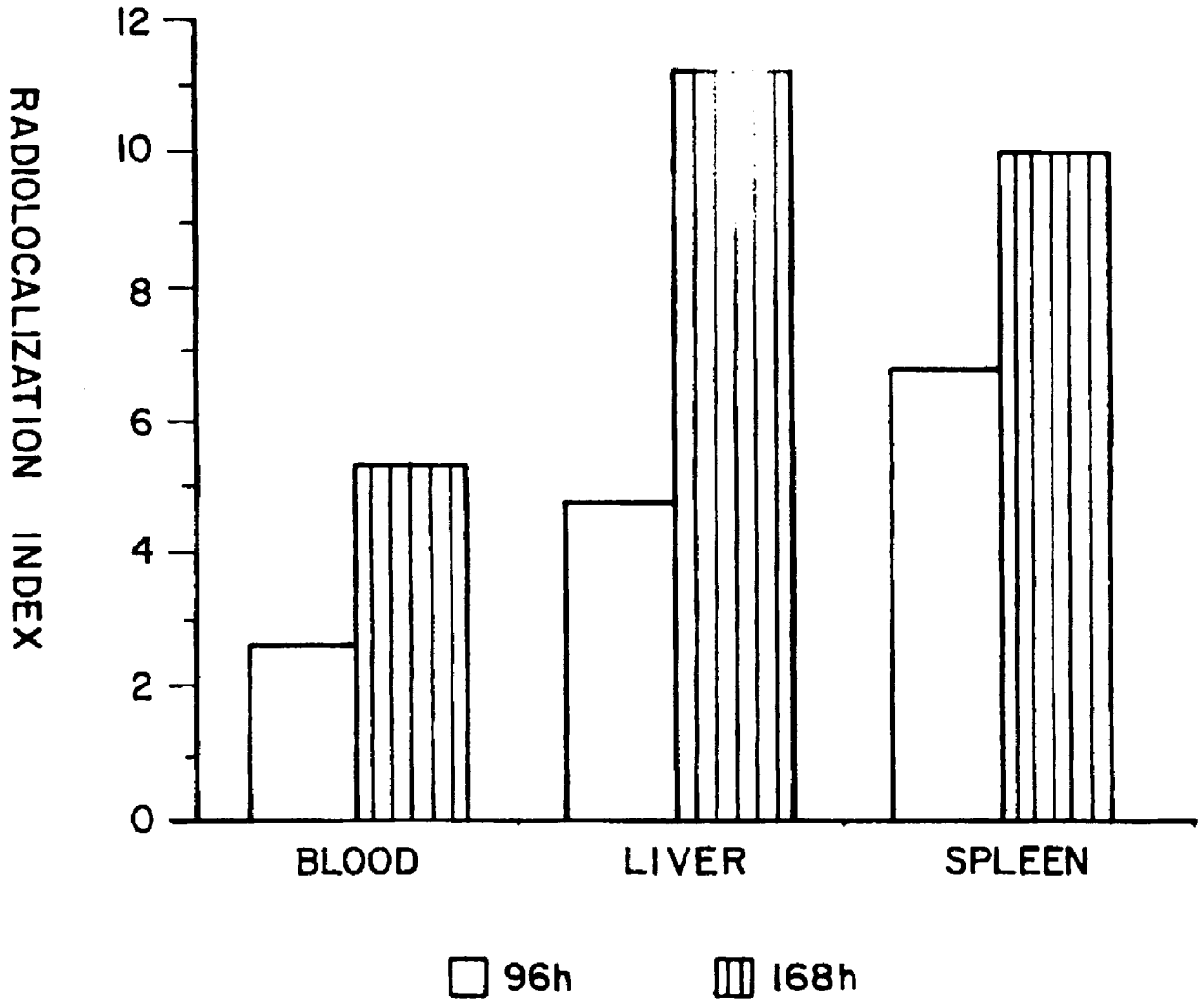
FIG. 3 is a graph showing the biodistribution of mAb 31.1 in nude mice bearing a xenografted human tumor, LS-174T.
Figure 4:
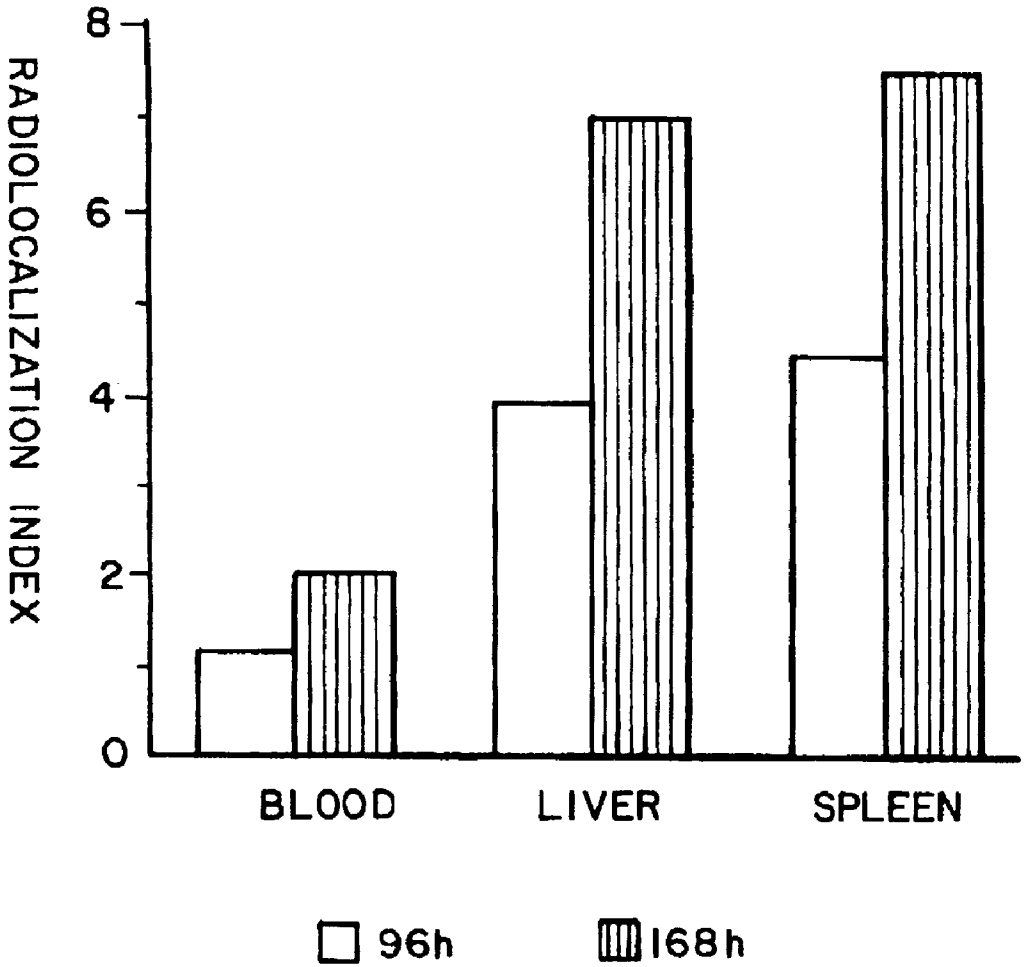
FIG. 4 is a graph showing the biodistribution of mAb 33.28 in nude mice bearing a xenografted human tumor, LS-174T.

The in vivo behavior of the mAbs of the present invention was examined by pharmacokinetic studies using $^{125}$I-labelled mAb and athymic nude mice bearing LS-174T colon tumor xenografts. Mice implanted with the A375 melanoma were employed as controls. The relative concentration of mAb in tumor as compared to adjacent normal tissue such as liver and spleen is represented by the radiolocalization index (concentration of radiolabelled material in tumor/concentration in surrounding tissue). The biodistribution of $^{125}$I-labelled 31.1 and 33.28 mAbs is shown in Table 9. Both mAbs were able to significantly concentrate within the tumor, compared to localization in normal tissues (spleen and liver). This selective accumulation was six-fold at 96 hours and about 12-fold at 168 hrs. The radiolocalization indices for both mAbs to tumor as compared to blood, liver and spleen are shown in FIG. 3 and FIG. 4.

TABLE 9

Biodistribution of $^{125}$I-mAbs in Tumor-Bearing Athymic Nude Mice

| | 96 hours | | 168 hours | |
|---|---|---|---|---|
| Tissue | LS174T | A375 | LS174T | A375 |
| A. mAb 31.1 | | | | |
| Blood | 7.30 | NA | 4.67 | 4.42 |
| Tumor | 21.92 | NA | 25.43 | 2.91 |
| Liver | 3.74 | NA | 2.16 | 1.24 |
| Spleen | 3.68 | NA | 2.41 | 1.32 |
| B. mAb 33.28 | | | | |
| Blood | 7.81 | NA | 5.58 | 3.95 |
| Tumor | 13.12 | NA | 15.50 | 2.24 |
| Liver | 2.55 | NA | 1.74 | 1.68 |
| Spleen | 2.31 | NA | 1.70 | 1.92 |

Results are expressed in % injected dose/gram of tissue.
LS174T = colon carcinoma; A375 = melanoma.

EXAMPLE X

Immunohistochemical Studies

The ability to detect tumor markers in the serum, image the related neoplastic process and define the cell population of that neoplasm by immunohistochemistry depends on the ability of specific mAbs to selectively characterize a tumor population.

The mAbs 31.1 and 33.28 were tested in more than 50 colon carcinomas by means of immunoperoxidase staining. They have been found to be highly reactive with the colon neoplasm and did not interact with the adjacent normal tissues. When polyps were evaluated, the wholly benign lesions such as villo-tubular adenomas showed no reactivity. Villous adenomas undergoing transformation reacted only at the site of malignancy. When similar tissues were evaluated using the more common carbohydrate-antigen derived mAbs, normal adjacent colon tissue reacted equally with the neoplastic portion of the specimen. With the 31.1 and 33.28 mAbs, each appeared to stain different cell populations within the tumor. This suggests that surface antigens representing different oncogene products were being defined.

EXAMPLE XI

Selective Binding to Subpopulations of Epithelial Cells in Paraffin-Embedded Benign and Malignant Mammary Lesions Forty-one formalin-fixed, paraffin-embedded benign and malignant breast specimens were studied with mAbs 31.1 and 33.28, using the avidin-biotin staining method. Without enzymatic pretreatment, positive staining of epithelium was observed on the cell surface and in the cytoplasm with both antibodies. 7/21 (33%) duct carcinogens were positive with mAb 31.1 as were 5/20 (25%) samples of benign breast disease. 10/21 (48%) duct carcinomas were positive with mAb 33.28 together with 7/20 (35%) specimens of benign mammary disease. 10 to 75% of the cell population was positively stained. These results indicate that the antigens defined by mAbs 31.1 and 33.28 are expressed in a select group of women with breast disease and would be useful for diagnosis of said disease.

EXAMPLE XII

Selective Binding to Subpopulations of Epithelial Cells in Fresh Frozen Benign and Malignant Ovarian Tumors Fresh frozen tissue biopsies obtained from twenty-one ovarian tumors subjected to immunocytochemical analysis were studied with mAbs 31.1 and 33.28 using the avidin biotin indirect immunoperoxidase assay. Focal positive staining was observed in 4/7 papillary mucous, 1/1 mucinous and ½ endometroid adenocarcinoma. None of the nonepithelial ovarian tumors stained positive using these monoclonal antibodies. These results indicate that the antigens as defined by mAbs 31.1 and 33.28 are expressed in a select group of woman with ovarian cancer and would be useful for diagnosis of said disease.

EXAMPLE XIII

Immunoreactivity of Human Carcinoma Tissues and Cell Lines with mAbs 31.1 and 33.28

The mAbs 31.1 and 33.28 were used to screen a panel of cell lines including colon adenocarcinoma, lymphoma, leukemia and neuroblastoma lines.

Using the avidin-biotin immunoperoxidase staining system, the mAbs 31.1 and 33.28 were shown to strongly bind to colon adenocarcinoma cell lines WIDR and HT-29. Immunoreactions were not observed with KG1-a, HL-60, Molt-3 and JUKRAT cell lines. Both antibodies reacted weakly with one lymphoma line (JY). The mAb 33.28 reacted weakly with one leukemic line (K562) and a neuroblastoma line (U87. MG). These results confirm and extend previous flow cytometry and immunofluorescent results in which it has been reported that strong binding reactions were observed with these mAbs with colon adenocarcinoma cell lines and reactions were not observed with other tumor cell lines. Using flow cytometry, mAb 31.1 reacted with 85% of HT-29 and WIDR colon carcinoma cells but not with SKBR-3 breast cancer cells.

Both antibodies were extensively shown to bind distinctively to colon carcinoma tissues (mAb 33.28–84%, mAb 31.1–64%), and not to normal tissues or malignant tissues including neuroblastoma tissues (0/3), lymphomas (0/3) and leukemic infiltrates (0/3) tested. These results suggest that these antibodies can serve as a useful research tool in evaluating tumor markers in cancer and cell biology research.

EXAMPLE XIV

Expression and Characterization of Chimeric Antibodies Against Human Colorectal Carcinoma-Associated Antigen A chimeric mouse/human heavy chain gene was constructed by splicing the exon of the 31.1 antibody heavy chain variable region gene to the exon of the human gamma1 chain contstant region gene using the polymerase chain reaction. Subsequently, the 31.1 chimeric gene was cloned into a retroviral expression vector pLgptCXII and transfected into the packaging cell line PA317. The transfected cells (PA317H) were cultivated with another packaging cell line PA317L, which contained an irrelevant mouse/human chimeric light chain gene in retroviral expression vector pLneoCXII, and SP2/0-Ag14 cells. The transduced SP2/0-Ag14 cells yielded a complete chimeric antibody. Chi #1 which reacted with horseradish peroxidase-conjugated igG of goat anti-human IgG Fc in ELISA analyses, which indicated that the constant region of Chi #1 was human. Cytofluorometry analysis indicated that Chi #1 stained human colorectal carcinoma cell lines HT-29 and LS174T but not a human lung carcinoma cell line A-427. Antibody-dependent cell-mediated cytoxicity (ADCC) assay indicated that Chi #1 lysed Ls174T cells. These results shows that Chi #1 retained the antigen-binding specificity of the parental 31.1 mouse monoclonal antibody, suggesting the useful of this chimeric antibody in ascertaining prognosis of colon carcinoma.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A monoclonal antibody specific for a purified human colon carcinoma-associated protein antigen, [wherein said antigen has the following characteristics:

(a) said antigen is purified to the extent that the membrane fractions are free of HL-A antigen and are substantially free from non-immunogenic glycoprotein fractions;

(b) said antigen is not detectable on normal colon cancer free human tissues;

(c) said antigen is not detectable on human carcinoma cells other than colon carcinoma cells;

(d) said antigen is specifically immunogenic in humans; and (e) said antigen induces an immune response in humans having colon carcinoma which is expressed as cell mediated immunity] *which is murine monoclonal antibody 33.28 as produced by hybridoma PCA 33.28, deposited with the American Type Culture Collection and assigned accession number PTA-5413.*

[2. An antibody according to claim 1 which is mouse monoclonal antibody 33.28 (ATCC HB-12315) or an antibody which binds specifically to a colon carcinoma-associated epitope that specifically binds to monoclonal antibody 3328.]

3. An antibody according to claim [2] *1* wherein said colon carcinoma-associated antigen is a protein having a molecular weight of about 61.1 kilodaltons *as measured by gradient polyacrylamide gel electrophoresis.*

4. [An antibody according claim 1] *A monoclonal antibody specific for a purified human colon carcinoma-associated protein antigen,* which is mouse monoclonal antibody *31.1, as produced by hybridoma PCA* 31.1 [(ATCC HB-12314)], *deposited with the American Type Culture Collection and assigned accession number PTA-2497*[or an antibody which binds specifically to a colon carcinoma-associated epitope that specifically binds to monoclonal antibody 31.1].

5. [An] *A monoclonal* antibody [according to claim 4 wherein said colon carcinoma-associated antigen is a protein having a molecular weight of about 72 kilodaltons] *which comprises an antigen-binding region obtained from the H chain of a murine monoclonal antibody 33.28 as produced by hybridoma PCA 33.28, deposited with the American Type Culture collection and assigned action number PTA-5413.*

6. An antibody according to claim [2] *1* wherein said colon carcinoma-associated antigen is a glycoprotien, the protein component having a molecular weight of 61.1 kilodaltons *as measured by gradient polyacrylamide gel electrophoresis.*

7. An antibody according to claim 1, *4 or 5* immobilized on a solid phase.

8. An antibody according to claim 1, *4 or 5* which is detectably labeled.

9. An antibody according to claim 8 wherein said detectable label is a radiolabel.

10. An antibody according to claim 1, *4 or 5* conjugated to a cytotoxic radionuclide.

11. An antibody according to claim 1, *4 or 5* conjugated to a cytotoxic drug.

12. An antibody according to claim 1, *4 or 5* conjugated to a cytotoxic protein.

13. A composition comprising an antibody according to claim 10 in combination with a pharmaceutically acceptable carrier.

14. A composition comprising an antibody according to claim 11 in combination with a pharmaceutically acceptable carrier.

15. A composition comprising an antibody according to claim 12 in combination with a pharmaceutically acceptable carrier.

[16. A monoclonal antibody against the monoclonal antibody of claim 1.]

[17. A monoclonal antibody against the monoclonal antibody of claim 2.]

[18. A monoclonal antibody against the monoclonal antibody of claim 3.]

[19. A monoclonal antibody against the monoclonal antibody of claim 4.]

[20. A monoclonal antibody against the monoclonal antibody of claim 5.]

[21. A monoclonal antibody against the monoclonal antibody of claim 6.]

22. An immunoassay for detecting a colon carcinoma-associated antigen which binds to mouse monoclonal antibody 33.28 [(ATCC HB-12315)] *as produced by hybridoma PCA 33.28, deposited with the American Type Culture Collection and assigned accession number PTA-5413,* in a sample comprising:

(a) contacting said sample with an effective binding amount of the antibody according to claim 1; and (b) detecting said antigen by detecting the binding of the antibody to the [purified] colon carcinoma-associated protein antigen.

23. An immunoassay for detecting a colon carcinoma-associated antigen which binds to mouse monoclonal antibody 31.1 [(ATCC HB-12314)], *as produced by hybridoma PCA 31.1, deposited with the American Type Culture Collection and assigned accession number PTA-2497,* in a sample comprising:

(a) contacting said sample with an effective binding amount of the antibody according to claim [1] *4 or claim 5*; and (b) detecting said antigen by detecting the binding of the antibody to the [purified] colon carcinoma-associated protein antigen.

24. A method for diagnosing colon cancer in humans comprising:

(a) removing a histological specimen from a patient suspected of having a colon cancer;

(b) contacting the specimen with monoclonal antibody 33.28 [(ATCC HB-12315)], *as produced by hybridoma PCA 33.28, deposited with the American Type Culture Collection and assigned accession number PTA-5413*;

(c) staining the specimen with an immunohistochemical stain; and (d) detecting the presence of the antigen-antibody complex by the stain.

25. A method for diagnosing colon cancer in humans comprising:

(a) removing a histological specimen from a patient suspected of having colon[-] carcinoma;

(b) contacting the specimen with mouse monoclonal antibody 31.1 [(ATCC HB-12314)], *as produced by hybridoma PCA 31.1, deposited with the American Type Culture Collection and assigned accession number PTA-2497*);

(c) staining the specimen with an immunohistochemical stain; and (d) detecting the presence of the antigen-antibody complex.

26. A method according to claim 24 wherein the stain is an avidin-biotin immunoperoxidase stain.

27. A method according to claim 25 wherein the stain is an avidin-biotin immunoperoxidase stain.

28. A kit for the immunohistochemical detection of colon carcinoma comprising:

(a) mouse monoclonal antibody 31.1 [(ATCC HB-12314)], *as produced by hybridoma PCA 31.1, deposited with the American Type Culture Collection and assigned accession number PTA-2497*;

(b) reagents for immunoperoxidase and secondary antibody;

(c) immunoperoxidase; and (d) colorizing reagents.

29. A kit for the immunohistochemical detection of colon carcinoma comprising:

(a) mouse monoclonal antibody 33.28 [(ATCC HB-12315], *as produced by hybridoma PCA 33.28, deposited with the American Type Culture Collection and assigned accession number PTA-5413*;

(b) reagents for immunoperoxidase and secondary antibody;

(c) immunoperoxidase; and (d) colorizing reagents.

[30. A compartmentalized kit for the detection of a human colon carcinoma-associated antigen, wherein the antigen has the following characteristics:

(a) said antigen is purified to the extent that the membrane fractions are free of HL-A antigen and are substantially free from non-immunogenic glycoprotein fractions;

(b) said antigen is not detectable on normal colon cancer free human tissues;

(c) said antigen is not detectable on human carcinoma cells other than colon carcinoma cells;

(d) said antigen is specifically immunogenic in humans; and (e) said antigen induces an immune response in humans having colon carcinoma which is expressed as cell mediated immunity, said kit comprising a first container adapted to contain an antibody to said antigen or an active component thereof, and a second container adapted to contain a second antibody to said antigen or an active component thereof, said second antibody being labeled with a reporter molecule capable of giving a detectable signal.]

[31. A kit according to claim 30 wherein the reporter molecule is a radioisotope, an enzyme, a fluorescent molecule, a chemiluminescent molecule or a bioluminescent molecule.]

[32. A kit according to claim 30 wherein the reporter molecule is an enzyme.]

[33. A kit according to claim 30 wherein the kit further comprises a third container adapted to contain a substrate for the enzyme.]

[34. A compartmentalized kit for the detection of a human colon carcinoma-associated antigen, wherein the antigen has the following characteristics:

(a) said antigen is purified to the extent that the membrane fractions are free of HL-A antigen and are substantially free from non-immunogenic glycoprotein fractions;

(b) said antigen is not detectable on normal colon cancer free human tissues;

(c) said antigen is not detectable on human carcinoma cells other than colon carcinoma cells;

(d) said antigen is specifically immunogenic in humans; and (e) said antigen induces an immune response in humans having colon carcinoma which is expressed as cell mediated immunity, said kit comprising a first container adapted to contain monoclonal antibody 31.1 (ATCC HB-12314) to said antigen and a second container adapted to contain a second antibody to said antigen or an active component thereof, said second antibody being labeled with a reporter molecule capable of giving a detectable signal.]

[35. A kit according to claim 34 wherein the reporter molecule is a radioisotope, an enzyme, a fluorescent molecule, a chemiluminescent molecule or a bioluminescent molecule.]

[36. A kit according to claim 32 wherein the reporter molecule is an enzyme.]

[37. A kit according to claim 33 wherein the kit further comprises a third container adapted to contain a substrate for the enzyme.]

[38. A compartmentalized kit for the detection of a human colon carcinoma-associated antigen, wherein the antigen has the following characteristics:

(a) said antigen is purified to the extent that the membrane fractions are free of HL-A antigen and are substantially free from non-immunogenic glycoprotein fractions;

(b) said antigen is not detectable on normal colon cancer free human tissues;

(c) said antigen is not detectable on human carcinoma cells other than colon carcinoma cells;

(d) said antigen is specifically immunogenic in humans; and (e) said antigen induces an immune response in humans having colon carcinoma which is expressed as cell mediated immunity, said kit comprising a first container adapted to contain monoclonal antibody 33.28 (ATCC HB-12315) to said antigen and a second container adapted to contain a second antibody to said antigen or an active component thereof, said second antibody being labeled with a reporter molecule capable of giving a detectable signal.]

[39. A kit according to claim 38 wherein the reporter molecule is a radioisotope, an enzyme, a fluorescent molecule, a chemiluminescent molecule or a bioluminescent molecule.]

[40. A kit according to claim 38 wherein the reporter molecule is an enzyme.]

[41. A kit according to claim 38 wherein the kit further comprises a third container adapted to contain a substrate for the enzyme.]

[42. The monoclonal antibody of claim 1 which is a chimeric antibody.]

43. [The] *A* chimeric antibody [according to claim 42] which is a chimeric mouse/human antibody Chi #1 *as produced by the cell line deposited with the American Type Culture Collection and assigned accession number* [(ATCC] CRL-12316[)].

[44. The chimeric antibody according to claim 42 wherein said colon carcinoma-associated antigen is a protein having a molecular weight of 72 kilodalton.]

45. A composition comprising the chimeric antibody according to claim [42] *43* in combination with a pharmaceutically acceptable carrier.

[46. A monoclonal antibody against the chimeric antibody of claim 42.]

47. An immunoassay for detecting a colon carcinoma-associated antigen which binds to the mouse/human chimeric antibody Chi #1 *as produced by the cell line deposited with the American Type Culture Collection and assigned accession number* [(ATCC] CRL-12316[) of claim 42] in a sample comprising:

(a) contacting said sample with the *Chi #1* antibody [according to claim 42]; and (b) detecting said antigen by detecting the binding of said antibody to the [purified] colon carcinoma-associated protein antigen.

48. A method for diagnosing colon cancer in humans comprising:

(a) removing a histological specimen from a patient suspected of having a colon carcinoma;

(b) contacting the specimen with a chimeric antibody [which binds to an antigen] according to claim [1] *43*;

(c) staining the specimen with an immunohistochemical stain; and (d) detecting the presence of the antigen-antibody complex by the stain.

49. A method for diagnosing colon cancer in humans comprising:

(a) removing a histological specimen from a patient suspected of having a colon carcinoma;

(b) contacting the specimen with mouse/human chimeric antibody which binds to an antigen which binds to mouse/human chimeric antibody Chi #1 [(ATCC] *as produced by the cell line deposited with the American Type Culture Collection and assigned accession number* CRL-12316[)];

(c) staining the specimen with an immunohistochemcial stain; and (d) detecting the presence of the antigen-antibody complex by the stain.

50. A kit for the immunohistochemical detection of colon carcinoma comprising:

(a) mouse/human chimeric antibody Chi #1 (ATCC CRL-12316);

(b) reagents for immunoperoxidase and secondary antibody;

(*c*) immunoperoxidase; and (d) colorizing reagents.

* * * * *